(12) United States Patent
Durgin et al.

(10) Patent No.: US 9,591,965 B2
(45) Date of Patent: Mar. 14, 2017

(54) ENDOSCOPES INCLUDING DISTAL CHAMBER AND RELATED METHODS OF USE

(75) Inventors: Russell F. Durgin, Bellingham, MA (US); Kenneth M. Blair, Burlington, MA (US); F. Anthony Headley, Jr., Plymouth, MN (US); Dennis R. Boulais, Danielson, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2316 days.

(21) Appl. No.: 12/078,963

(22) Filed: Apr. 8, 2008

(65) Prior Publication Data
US 2008/0255424 A1    Oct. 16, 2008

Related U.S. Application Data

(60) Provisional application No. 60/907,580, filed on Apr. 10, 2007.

(51) Int. Cl.
| | | |
|---|---|---|
| *A61B 1/00* | (2006.01) | |
| *A61B 1/012* | (2006.01) | |
| *A61B 10/06* | (2006.01) | |
| *A61B 1/04* | (2006.01) | |
| *A61B 10/00* | (2006.01) | |
| *A61B 10/02* | (2006.01) | |
| *A61B 17/34* | (2006.01) | |
| *A61B 17/29* | (2006.01) | |

(52) U.S. Cl.
CPC ............ *A61B 1/012* (2013.01); *A61B 1/0008* (2013.01); *A61B 10/06* (2013.01); *A61B 90/98* (2016.02); *A61B 10/0096* (2013.01); *A61B 10/0283* (2013.01); *A61B 17/3462* (2013.01); *A61B 2010/0225* (2013.01); *A61B 2017/2931* (2013.01); *A61B 2090/0811* (2016.02)

(58) Field of Classification Search
USPC ........ 600/127, 129, 153, 155–158, 114, 115, 600/116
See application file for complete search history.

(56) References Cited

U.S. PATENT DOCUMENTS

| | | | | |
|---|---|---|---|---|
| 3,720,203 | A * | 3/1973 | Brown | 600/184 |
| 4,832,024 | A * | 5/1989 | Boussignac et al. | 606/7 |
| 4,878,485 | A * | 11/1989 | Adair | 600/122 |
| 6,354,992 | B1 * | 3/2002 | Kato | 600/157 |
| 6,520,939 | B2 * | 2/2003 | Lafontaine | 604/167.03 |

(Continued)

FOREIGN PATENT DOCUMENTS

| | | |
|---|---|---|
| EP | 1 736 103 A1 | 12/2006 |
| JP | 06-054801 | 1/1994 |

(Continued)

OTHER PUBLICATIONS

International Search Report for PCT/US2008/059769 dated Aug. 12, 2008.

(Continued)

*Primary Examiner* — Timothy J Neal
(74) *Attorney, Agent, or Firm* — Bookoff McAndrews, PLLC

(57) ABSTRACT

Embodiments of the invention include an endoscope including a distal chamber and related methods of use, for example, with an endoscopic instrument.

26 Claims, 18 Drawing Sheets

(56) References Cited

U.S. PATENT DOCUMENTS 7,860,555 B2 * 12/2010 Saadat ........................ 600/476
2003/0105386 A1 * 6/2003 Voloshin et al. ............. 600/114

FOREIGN PATENT DOCUMENTS

| WO | WO 01/58360 A2 | 8/2001 |
| WO | WO 2006/124489 A1 | 11/2006 |
| WO | WO 2007/011040 A1 | 1/2007 |

OTHER PUBLICATIONS

Written Opinion of the International Searching Authority for PCT/US2008/059769 dated Aug. 12, 2008.

* cited by examiner

ENDOSCOPES INCLUDING DISTAL CHAMBER AND RELATED METHODS OF USE

CROSS-REFERENCE TO RELATED APPLICATION

This patent application claims the benefit of priority under 35 U.S.C. §119 to U.S. Provisional Patent Application No. 60/907,580, entitled ENDOSCOPES INCLUDING DISTAL CHAMBER AND RELATED METHODS OF USE, filed on Apr. 10, 2007, the entirety of which is incorporated herein by reference.

DESCRIPTION OF THE INVENTION

Field of the Invention

Embodiments of the invention include an endoscope including a distal chamber and related methods of use, for example, with an endoscopic instrument.

Background of the Invention

Endoscopes may be used with endoscopic instruments to treat the body. For example, an endoscope may be advanced into a patient's body lumen, such as a portion of a gastrointestinal tract like a colon. An endoscopic instrument, for example, a biopsy forceps instrument, may then be advanced down a working lumen of the endoscope, out a distal end of the endoscope, and into the gastrointestinal tract. The endoscope may then be maneuvered to a particular portion of the colon from which a tissue sample is desired, and the biopsy forceps instrument may then obtain a tissue sample from the colon. Once the tissue sample has been acquired, the biopsy forceps instrument may be retracted out of the endoscope, and the tissue sample may then be removed from the biopsy forceps instrument. The tissue sample is then placed in a container and labeled. Once the tissue sample has been removed, the procedure may be repeated by advancing the biopsy forceps instrument back down the working lumen of the endoscope into the gastrointestinal tract. For example, to diagnose inflammatory bowel disease, 20 or more tissue samples may be required from the colon.

This procedure is time consuming, especially when using long, flexible endoscopes, such as colonoscopes. Sometimes, multiple samples can be obtained during one passage of the biopsy forceps instrument through the endoscope lumen, by stacking samples inside the biopsy jaws.

SUMMARY OF THE INVENTION

An embodiment of the invention may include an endoscope. The endoscope may include an elongate member, at least two lumens extending through the elongate member, and a chamber defined by a distal portion of the elongate member. A distal end of each of the at least two lumens may terminate in the chamber.

Various embodiments of the invention may include one or more of the following aspects: wherein the chamber is configured to accommodate a distal assembly of a medical instrument; wherein the chamber includes a first seal at a distal end of the chamber and a second seal at a proximal end of the chamber.

Another embodiment of the invention may include an endoscope. The endoscope may include an elongate member, an irrigation lumen and an aspiration lumen extending through the elongate member, and a chamber defined by a distal portion of the elongate member. A distal end of each of the irrigation lumen and the aspiration lumen may terminate in the chamber. The chamber may be configured to accommodate a distal assembly of a medical instrument.

Various embodiments of the invention may include one or more of the following aspects: wherein the distal ends of each of the irrigation lumen and the aspiration lumen are at an angle relative to a longitudinal axis of the elongate member; wherein the chamber includes a first seal at a distal end of the chamber and a second seal at a proximal end of the chamber; wherein at least one of the irrigation lumen and the aspiration lumen includes a valve configured to selectively provide irrigation or aspiration, respectively, to either the chamber or a body lumen; and wherein a distal end of at least one of the irrigation lumen and the aspiration lumen includes a nozzle-like configuration or a flare-like configuration.

A further embodiment of the invention may include an endoscope. The endoscope may include an elongate member, an irrigation lumen extending through the elongate member, and a chamber defined by a distal portion of the elongate member. A distal end of the irrigation lumen may terminate in the chamber. The chamber may be configured to accommodate a distal assembly of a medical instrument.

Various embodiments of the invention may include one or more of the following aspects: wherein the chamber includes a first seal at a distal end of the chamber and a second seal at a proximal end of the chamber; wherein the chamber includes a first seal at a distal end of the chamber and a second seal on the medical instrument; wherein the irrigation lumen is configured to selectively provide irrigation to either the chamber or a treatment site; a sensor configured to detect an entrance of the distal assembly into the chamber; and wherein the irrigation lumen is configured to accommodate the medical instrument therethrough.

Yet another embodiment of the invention may include an endoscope. The endoscope may include an elongate member, at least two lumens extending through the elongate member, and a chamber defined by a distal portion of the elongate member. A distal end of each of the at least two lumens may terminate in the chamber. A seal may be disposed between a distal end of at least one of the at least two lumens and the chamber.

Various embodiments of the invention may include the following aspect: wherein the chamber is configured to accommodate a distal assembly of a medical instrument.

A yet further embodiment of the invention may include an endoscope. The endoscope may include an elongate member, at least two lumens extending through the elongate member, and a chamber defined by a distal portion of the elongate member. A distal end of each of the at least two lumens may terminate in the chamber. The chamber may include a first seal at a distal end of the chamber and a second seal at a proximal end of the chamber.

Various embodiments of the invention may include the following aspect: wherein the chamber is configured to accommodate a distal assembly of a medical instrument in an open configuration.

Still another embodiment of the invention may include a method. The method may include providing an endoscope including an elongate member, the elongate member including an irrigation lumen, an aspiration lumen, a working lumen, and a chamber defined by a distal portion of the elongate member, a distal end of each of the irrigation lumen, the aspiration lumen, and the working lumen terminating in the chamber, providing a medical instrument, advancing the elongate member of the endoscope through a body lumen, advancing the medical instrument through the working lumen of the endoscope, through the chamber, out of a distal end of the endoscope, and into the body lumen, obtaining a tissue sample with the medical instrument, placing the tissue sample in the chamber, and removing the medical instrument and the endoscope from the body lumen.

Various embodiments of the invention may include one or more of the following aspects: providing irrigation fluid to the chamber via the irrigation lumen; providing suction to the aspiration lumen so as to aspirate the tissue sample from the chamber; providing irrigation fluid to the chamber via the irrigation lumen; placing the tissue sample in a collection container without removing the medical instrument from the endoscope; wherein the step of placing the tissue sample occurs after the step of providing suction to the aspiration lumen; wherein the distal ends of each of the irrigation lumen and the aspiration lumen are at an angle relative to a longitudinal axis of the elongate member; wherein the chamber includes a first seal at a distal end of the chamber and a second seal at a proximal end of the chamber; advancing the medical instrument through the first seal and the second seal; obtaining a second tissue sample without removing the medical instrument from the endoscope; selectively irrigating at least one of the chamber and the body lumen via the irrigation lumen; selectively aspirating at least one of the chamber and the body lumen via the aspiration lumen; and sensing an entrance of the medical instrument into the chamber.

A still further embodiment of the invention may include a method. The method may include providing an endoscope including an elongate member, the elongate member including an aspiration lumen, a working lumen, and a chamber defined by a distal portion of the elongate member, a distal end of each of the aspiration lumen and the working lumen terminating in the chamber, providing a medical instrument including a distal assembly, advancing the elongate member of the endoscope through a body lumen, advancing the distal assembly of the medical instrument through the working lumen of the endoscope, through the chamber, out of a distal end of the endoscope, and into the body lumen, obtaining a tissue sample with the distal assembly, retracting the medical instrument so as to place the distal assembly and the tissue sample in the chamber, and removing the medical instrument and the endoscope from the body lumen.

Various embodiments of the invention may include one or more of the following aspects: providing suction to the aspiration lumen so as to aspirate the tissue sample from the chamber; wherein the chamber includes a first seal at a distal end of the chamber and a second seal at a proximal end of the chamber; advancing the distal assembly through the first seal and the second seal; further comprising obtaining a second tissue sample without removing the medical instrument from the endoscope; placing the tissue sample in a collection container without removing the medical instrument from the endoscope; wherein the step of placing the tissue sample occurs after the step of providing suction to the aspiration lumen; selectively aspirating at least one of the chamber and the body lumen via the aspiration lumen; and sensing an entrance of the distal assembly into the chamber.

Another embodiment of the invention may include a method. The method may include providing an endoscope including an elongate member, the elongate member including an aspiration lumen, a working lumen, and a chamber defined by a distal portion of the elongate member, a distal end of each of the aspiration lumen and the working lumen terminating in the chamber. The chamber may include a proximal seal disposed between the chamber and the working lumen and a distal seal disposed between the chamber and an outside environment. The method may further include providing a medical instrument including a distal assembly, advancing the elongate member of the endoscope through a body lumen, advancing the distal assembly of the medical instrument through the working lumen of the endoscope, through the proximal seal, through the chamber, through the distal seal, out of a distal end of the endoscope, and into the body lumen, obtaining a tissue sample with the distal assembly of the medical instrument, retracting the distal assembly through the distal seal so as to place the distal assembly of the medical instrument and the tissue sample in the chamber, and removing the medical instrument and the endoscope from the body lumen.

Various embodiments of the invention may include one or more of the following aspects: providing suction to the aspiration lumen so as to aspirate the tissue sample from the chamber; placing the tissue sample in a collection container without removing the medical instrument from the endoscope; wherein the step of placing the tissue sample occurs after the step of providing suction to the aspiration lumen; obtaining a second tissue sample without removing the medical instrument from the endoscope; selectively aspirating at least one of the chamber and the body lumen via the aspiration lumen; and sensing an entrance of the distal assembly into the chamber.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1 also includes an endoscopic instrument disposed through the endoscope.

DESCRIPTION OF THE EMBODIMENTS

Figure 1:
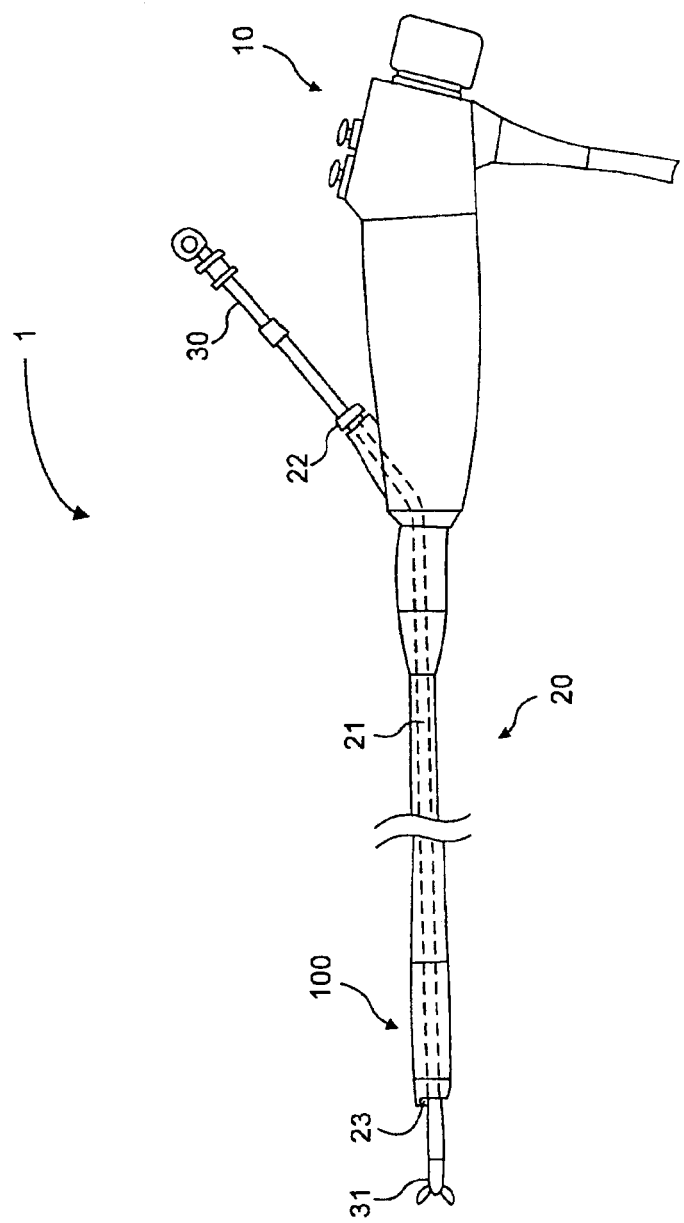
FIG. 1 is a schematic view of an endoscope according to an embodiment of the invention.

Reference will now be made in detail to exemplary embodiments of the invention, examples of which are illustrated in the accompanying drawings. Wherever possible, the same reference numbers will be used throughout the drawings to refer to the same or like parts.

FIGS. 1-4 depict an exemplary embodiment of an endoscope 1. Endoscope 1 may include a handle portion 10, an elongate member 20, and a distal portion 100, however, endoscope 1 may have any other suitable endoscopic components and/or configurations.

Elongate member 20 may have a plurality of lumens 21 running therethrough, for example, an irrigation lumen, an aspiration lumen, and a working lumen. Each lumen 21 may have a proximal end 22 and a distal end 23. Elongate member 20 may be configured to have an endoscopic instrument 30 extending therethrough, for example, through lumen 21 between proximal end 22 and distal end 23. Each lumen 21 within elongate member 20 may mate with a corresponding portion of distal portion 100. Distal portion 100 may be integrally formed with elongate member 20.

Endoscopic instrument 30 may include distal assembly 31, for example, a biopsy forceps device having a pair of jaws for obtaining a tissue sample.

Figure 4:
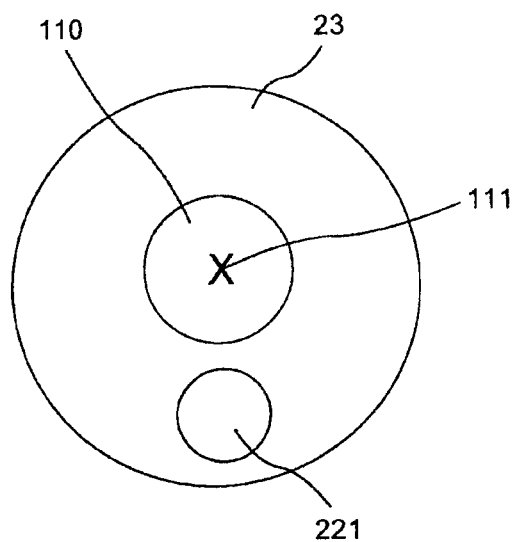
FIG. 4 is a schematic cross-sectional view of a distal portion of the endoscope of FIG. 1.

Endoscope 1 may also including a viewing lumen 221, as shown in FIG. 4, extending through elongate member 20 and extending to handle portion 10. Viewing lumen 221 may be configured, for example, to allow an operator to view an operative site through distal end 23 using any suitable visual apparatus and/or method.

Figure 2:
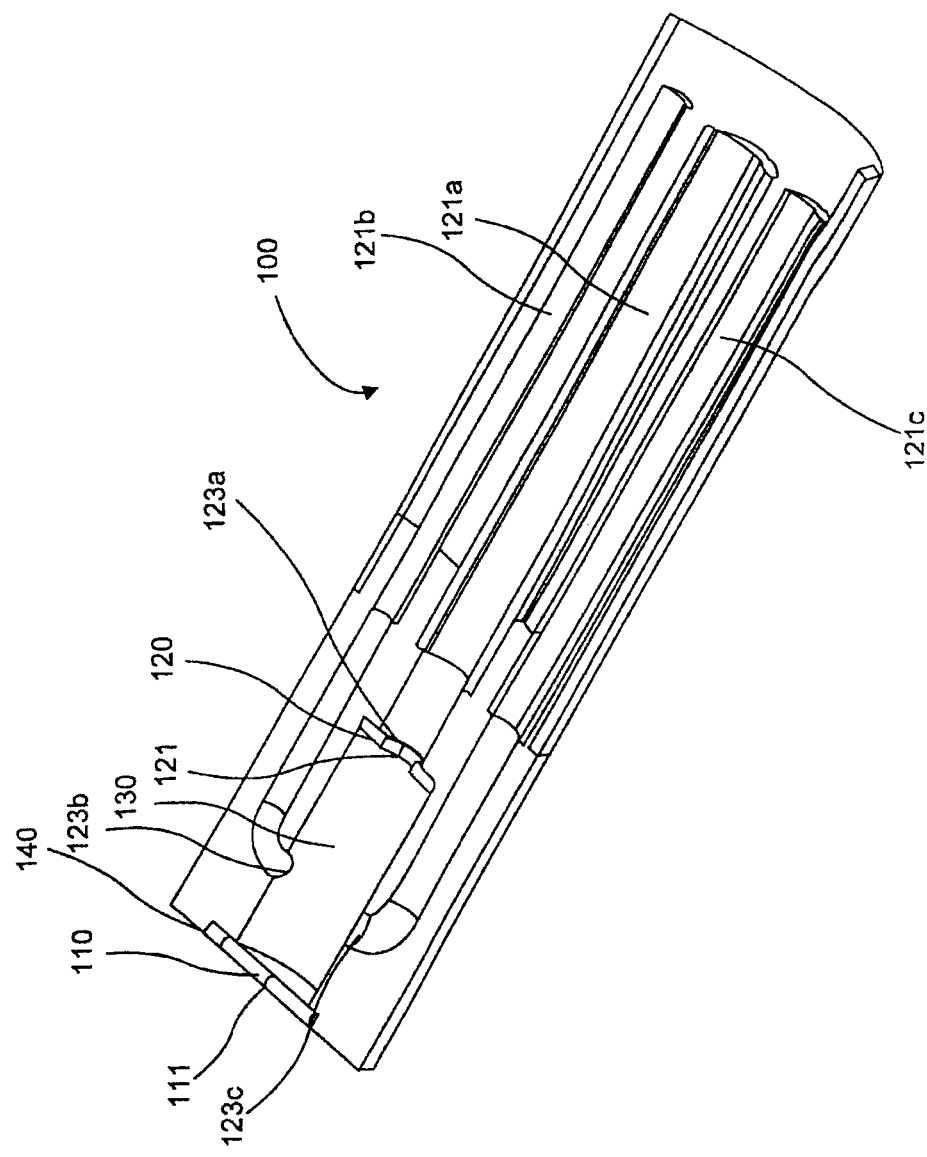
FIG. 2 is a schematic cross-sectional view of a distal portion of the endoscope of FIG. 1.

An exemplary longitudinal cross-section of distal portion 100 of endoscope 1 is shown in FIG. 2. Distal portion 100 may be removable from elongate portion 20 of endoscope 1 or may be integrally formed with elongate member 20. Distal portion 100 may include one or more of working lumen 121a, irrigation lumen 121b, and aspiration lumen 121c. In various embodiments, the functions of any irrigation lumen and any aspiration lumen set forth in this application may be interchangeable (e.g., irrigation and/or aspiration may be conducted through any irrigation lumen, and irrigation and/or aspiration may be conducted through any aspiration lumen). Each of working lumen 121a, irrigation lumen 121b, and aspiration lumen 121c may include a respective distal end 123a, 123b, 123c that terminates in a distal chamber 130. Distal chamber 130 may be bounded by a first seal 110 and a second seal 120, for example, on its distal and proximal ends, respectively. Distal portion 100 may also include a sensor 140. Any portion of distal portion 100 may be made of any suitable biocompatible materials, for example, rigid materials configured to resist deformation in a body lumen and without damaging the body lumen.

Working lumen 121a may be substantially parallel to a longitudinal axis of elongate member 20 and/or distal portion 100. Working lumen 121a may be configured to allow endoscopic instrument 30 to be advanced therethrough, for example, a distal assembly 31 including a biopsy forceps device. Working lumen 121a may be have a substantially circular cross-section, however, working lumen 121a may have any suitable shape, size, and/or configuration. Distal assembly 31 of endoscopic instrument 30 may be inserted through a proximal end 122a of working lumen 121a and emerge in distal chamber 130 via distal end 123a.

Although the illustrated embodiment of endoscope 1 is depicted as having one working lumen 121a, those having ordinary skill in the art will readily appreciate that endoscope 1 may include a plurality of working lumens or channels. For example, it is contemplated that endoscope 1 may be configured as a two-channel endoscope, so as to facilitate simultaneous insertion of a plurality of endoscopic instruments 30. In those embodiments where endoscope 1 includes a plurality of working lumens or channels, distal chamber 130 may be appropriately configured to be in communication with each of the plurality of working lumens or channels. For example, in those embodiments where endoscope 1 is configured as a two-channel endoscope, distal chamber 130 may be made larger to be in communication with both working channels.

Most of each of irrigation lumen 121b and aspiration lumen 121c may be substantially parallel to a longitudinal axis of elongate member 20, distal portion 100, and/or working lumen 121a. Most of each of irrigation lumen 121b and aspiration lumen 121c may also be substantially parallel to each other. Each of irrigation lumen 121b and aspiration lumen 121c may have a substantially circular cross-section, however, each of irrigation lumen 121b and aspiration lumen 121c may have any suitable shape, size, and/or configuration.

Figure 3:
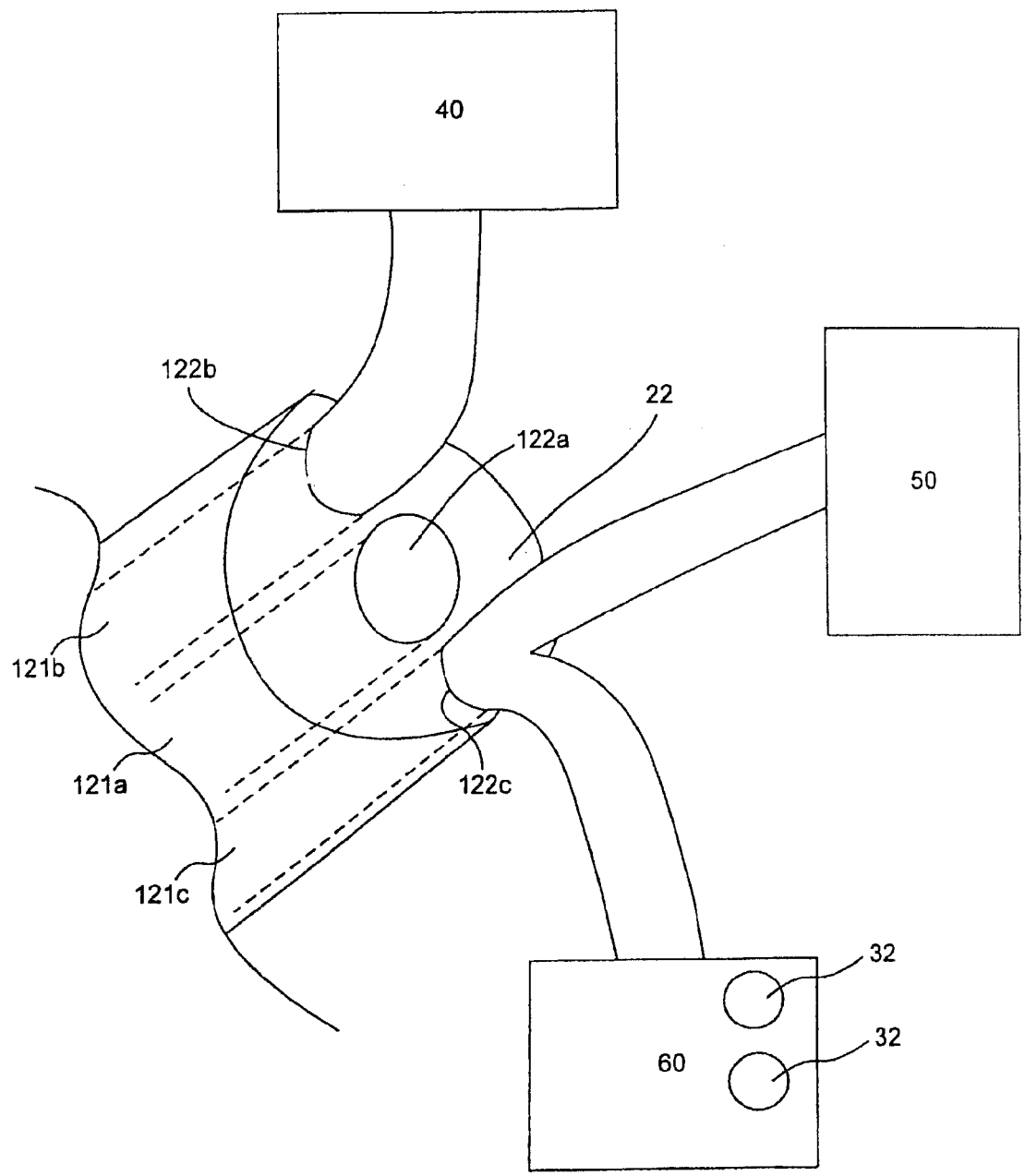
FIG. 3 is a schematic view of a proximal portion of the endoscope of FIG. 1.

Irrigation lumen 121b may be configured to facilitate fluid flow therethrough, for example, from a proximal end 122b to distal end 123b and into distal chamber 130. Proximal end 122b may be configured to be attached to a source of fluid 40, for example, as shown in FIG. 3. A portion of irrigation lumen 121b proximal to distal end 123b may be curved so that lumen 121b leads to chamber 130. A line normal to a plane defining distal end 123b may form an angle with a longitudinal axis of one or more of elongate member 20, distal portion 100, and/or working lumen 121a, for example, substantially a right angle. Distal end 123b of irrigation lumen 121b may have a narrow exit, be configured in the shape of a nozzle (e.g., decreasing in cross-sectional diameter closer to chamber 130), and/or have any other configuration to alter fluid flow, for example, into chamber 130.

Aspiration lumen 121c may be configured to facilitate suction and/or fluid flow therethrough, for example, to remove a tissue sample 32 and/or fluid from distal chamber 130, through distal end 123c, and to a proximal end 122c. Proximal end 122c may be configured to be attached to a source of suction 50 and/or a container 60 configured, for example, to collect tissue samples 32, for example, as shown in FIG. 3. Source of suction 50 and container 60 may be arranged in any suitable configuration. A portion of aspiration lumen 121c proximal to distal end 123c may be curved so that lumen 121c leads to chamber 130. A line normal to a plane defining distal end 123c may form an angle with a longitudinal axis of one or more of elongate member 20, distal portion 100, and/or working lumen 121a, for example, substantially a right angle. Distal end 123c of aspiration lumen 121c may be configured to ease fluid flow and/or entry of biopsy sample 32 from chamber 130, for example, by being flared (e.g., increasing in cross-sectional diameter closer to chamber 130).

The flow of fluid within irrigation lumen 121b and aspiration lumen 121c may be in substantially opposite directions. For example, fluid may flow through irrigation lumen 121b in a substantially distal direction while fluid and/or tissue samples may flow through aspiration lumen 121c in substantially a proximal direction. Fluid flow through irrigation lumen 121b and aspiration lumen 121c may be independently operated such that they are in operation at the same time, or at different times (e.g., staggered flow). For example, fluid may flow to distal chamber 130 via irrigation lumen 121b prior to aspiration being conducted via aspiration lumen 121c, so as to float tissue sample 32 in fluid and allow it to be more easily aspirated out of distal chamber 130. The fluid flowing from irrigation lumen 121b to aspiration lumen 121c may serve as both a carrier to advance tissue sample 32 through aspiration lumen 121c to container 60 and a lubricant to reduce friction between a wall of aspiration lumen 121c and tissue sample 32.

Figure 5:
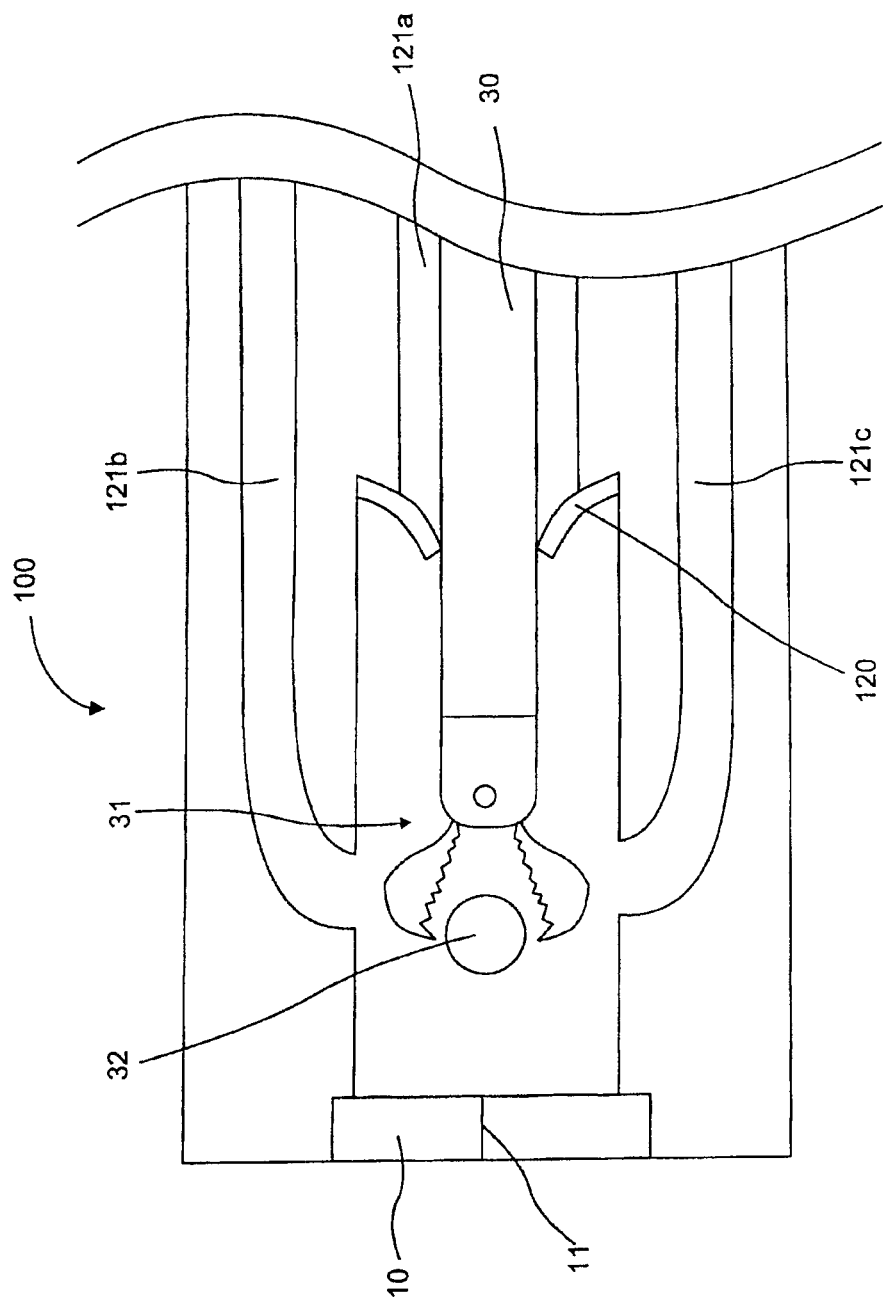
FIG. 5 is a schematic view of a distal assembly of an endoscopic instrument disposed in the distal portion of FIG. 2 of the endoscope of FIG. 1.

Distal chamber 130 may have a substantially cylindrical shape, and may be in flow communication with one or more of working lumen 121a, irrigation lumen 121b, and aspiration lumen 121c via respective distal ends 123a, 123b, 123c. For example, distal chamber 130 may be configured to receive endoscopic instrument 30 from working lumen 121a via distal end 123a, fluid from irrigation lumen 121b via distal end 123b, and/or suction from aspiration lumen 121c via distal end 123c. Distal chamber 130 may sized to surround an entirety of distal assembly 31 of endoscopic instrument 30, for example, a portion of a biopsy forceps device that includes an acquired tissue sample 32. Distal chamber 130 may also be sized to accommodate distal assembly 31 in an open configuration such that an acquired tissue sample 32 may be removed from endoscopic instrument 30, for example, as shown in FIG. 5. In various embodiments, however, distal chamber 130 may have any suitable shape, size, and/or configuration. For example, at least a portion of distal chamber 130 may have a cross-sectional area substantially the same as endoscopic instrument 30 in a closed configuration. Thus, when endoscopic instrument 30 is withdrawn into distal chamber 130 and contacts the aforementioned portion of distal chamber 130, such physical contact may provide a tactile indication to a user that endoscopic instrument 30 is disposed in distal chamber 130.

First seal 110 may be disposed between distal chamber 130 and the outside environment (e.g., a treatment site within a body lumen), and may have any suitable configuration and may be made of any suitable biocompatible material. First seal 110 may also be disposed between distal ends 123a, 123b, 123c of respective working lumen 121a, irrigation lumen 121b, and/or aspiration lumen 121c and the outside environment. Distal assembly 31 of endoscopic instrument 30 may be passed from distal chamber 130 to the outside environment through first seal 110, for example, via a perforation 111 in first seal 110, such as slits in an elastomeric seal. When endoscopic instrument 30 is disposed through first seal 110, first seal 110 may form a substantially fluid tight fit around a portion of endoscopic instrument 30, for example, to prevent fluid flow into and/or out of distal chamber 130 via first seal 110. First seal 110 may be configured to inhibit fluid flow between distal chamber 130 and the outside environment, for example, when aspiration lumen 121c is performing aspiration on distal chamber 130, whether or not endoscopic instrument 30 is disposed through first seal 110. Fluid flowing from irrigation lumen 121b into distal chamber 130 may be inhibited from flowing to the outside environment by first seal 110, also whether or not endoscopic instrument 30 is disposed through first seal 110.

Second seal 120 may be disposed between distal chamber 130 and distal end 123a of working lumen 121a, and may have any suitable configuration and may be made of any suitable biocompatible material. Second seal 120 may also be disposed between distal ends 123b, 123c of respective irrigation lumen 121b and/or aspiration lumen 121c and distal end 123a of working lumen 121a. Distal assembly 31 of endoscopic instrument 30 may be passed into distal chamber 130 through second seal 120, for example, via a perforation 121 in second seal 120, such as slits in an elastomeric seal. When endoscopic instrument 30 is disposed through second seal 120, second seal 120 may form a substantially fluid tight fit around a portion of endoscopic instrument 30, for example, to prevent fluid flow into and/or out of distal chamber 130 via second seal 120. Second seal 120 may be configured to inhibit fluid flow between distal chamber 130 and working lumen 121a, for example, when aspiration lumen 121c is performing aspiration on distal chamber 130, whether or not endoscopic instrument 30 is disposed through second seal 120. Fluid flowing from irrigation lumen 121b into distal chamber 130 may be inhibited from flowing into working lumen 121a by second seal 120, also whether or not endoscopic instrument 30 is disposed through second seal 120.

First seal 110 and second seal 120 may be configured to prevent air or other fluids from the outside environment and/or working lumen 121a from entering distal chamber 130, for example, while aspiration lumen 121c is removing air, fluid, and/or tissue samples from distal chamber 130. Accordingly, suction from distal chamber 130 via aspiration lumen 121c may be enhanced. First seal 110 and second seal 120 may also or alternatively be configured to prevent fluid and/or biopsy samples from exiting distal chamber 130 to the outside environment and/or working lumen 121a.

First seal 110 and second seal 120 may be made out of any suitable biocompatible material, for example, an elastomer, silicone, or polyurethane. Some examples of seals include RX (Rapid Exchange) LOCKING DEVICE AND BIOPSY CAP SYSTEM™ manufactured by BOSTON SCIENTIFIC CORPORATION™ or any of its subsidiaries.

Sensor 140 may be configured to allow a user to determine when distal assembly 31 of endoscopic instrument 30 is no longer disposed in the outside environment, and instead is disposed in distal chamber 130. For example, sensor 140 may be coupled to one or more of distal chamber 130, first seal 110, and second seal 120 to provide audio or visual feedback to the user by detecting the presence of distal assembly 31 in distal chamber 130 using any suitable method. Some suitable sensors 140 may include a sensor which utilizes magnets (e.g., to produce a Hall effect), broken light beams, or RFID sensors. However, any suitable sensor 140 may be used. Sensor(s) 140 may located on any suitable portion of endoscope 1 and/or endoscopic instrument 30 depending on the type of sensor used.

In the alternative, the user may be provided with sufficient tactile feedback when the distal assembly 31 enters distal chamber 130 so as to make sensor 140 unnecessary. For example, the user may be able to feel on the proximal end of endoscopic instrument 30 when distal assembly 31 completely enters distal chamber 130 because distal assembly 31 will no longer be disposed through, and hence disengage from, first seal 110.

In a further embodiment where sensor(s) 140 may not be necessary, endoscopic instrument 30 may have visual markers or other indicators on its proximal end. Such visual markers or other indicators may be configured such that when endoscopic instrument 30 is disposed in distal chamber 130, the visual marker or other indicators emerge from proximal end 122a of working lumen 121a.

Figure 10:
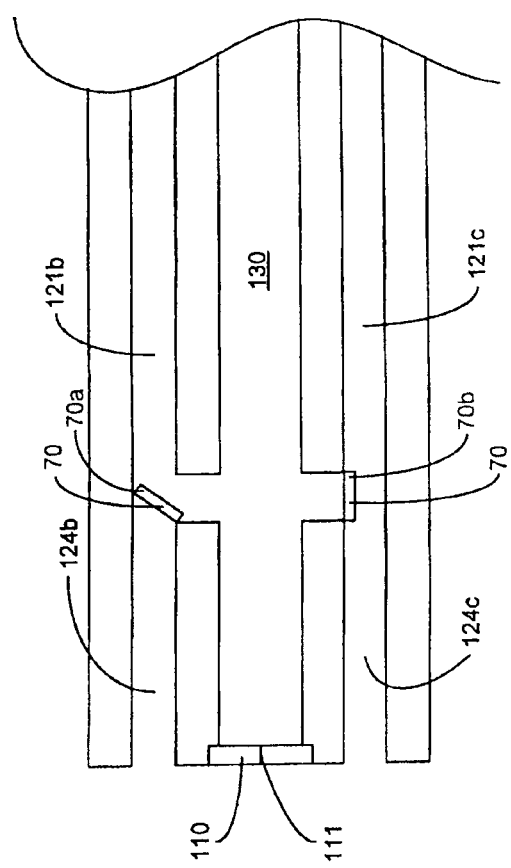
FIG. 10 is a schematic view of a distal portion of an endoscope according to a still further embodiment of the invention.

FIG. 10 depicts an exemplary embodiment of endoscope 1 including one or more valves 70. Valves 70 may be configured to selectively direct irrigation and/or suction to/from at least one of the outside environment and distal chamber 130. For example, endoscope 1 may include irrigation valve 70a and aspiration valve 70b.

Irrigation valve 70a may be disposed in irrigation lumen 121b and may be configured to, in a first position, allow fluid flow from irrigation lumen 121b to chamber 130 and at least partially prevent fluid flow from irrigation lumen 121b to the outside environment via irrigation extension 124b, and, in a second position, allow fluid flow from irrigation lumen 121b to the outside environment via irrigation extension 124b and at least partially prevent fluid flow from irrigation lumen 121b to chamber 130. In FIG. 10, irrigation valve 70a is disposed in the first position. Accordingly, a user may selectively irrigate either chamber 130 or the outside environment depending on the position of irrigation valve 70a.

Aspiration valve 70b may be disposed in aspiration lumen 121c and may be configured to, in a first position, allow suction from chamber 130 to aspiration lumen 121c and prevent suction from the outside environment to aspiration lumen 121c via aspiration extension 124c, and, in a second position, allow suction from the outside environment to aspiration lumen 121c via aspiration extension 124c and substantially prevent suction from chamber 130 to aspiration lumen 121c. In FIG. 10, aspiration valve 70b is disposed in the second position. Accordingly, a user may selectively suction either chamber 130 or the outside environment depending on the position of aspiration valve 70b.

Valves 70 may be any suitable valves and may be selectively and/or independently actuated using any suitable control mechanism. For example, valves 70 may be a poppet or flapper type valve that is connected to an actuation wire that runs along and/or through elongate member 20 to handle portion 10. In another example, valves 70 may be miniaturized solenoid valves actuated using any suitable method, for example, electrical, infrared, or wireless structures. Handle portion 10 may have suitable actuators for the user to actuate valves 70 into the appropriately desired position. One advantage of valves 70 may be that it may reduce the number of lumens in endoscope 1 by allowing irrigation lumen 121b to provide fluid to both the outside environment and chamber 130. The same is true for aspiration lumen 121c and suction. In an alternative embodiment, sliding windows may be used to selectively control fluid flow and/or biopsy sample suction into and out of irrigation lumen 121b and/or aspiration lumen 121c. For example, a sliding window may be configured to slide distally to cover distal end 123b, 123c of lumen 121b, 121c, and proximally to uncover them.

Figure 11:
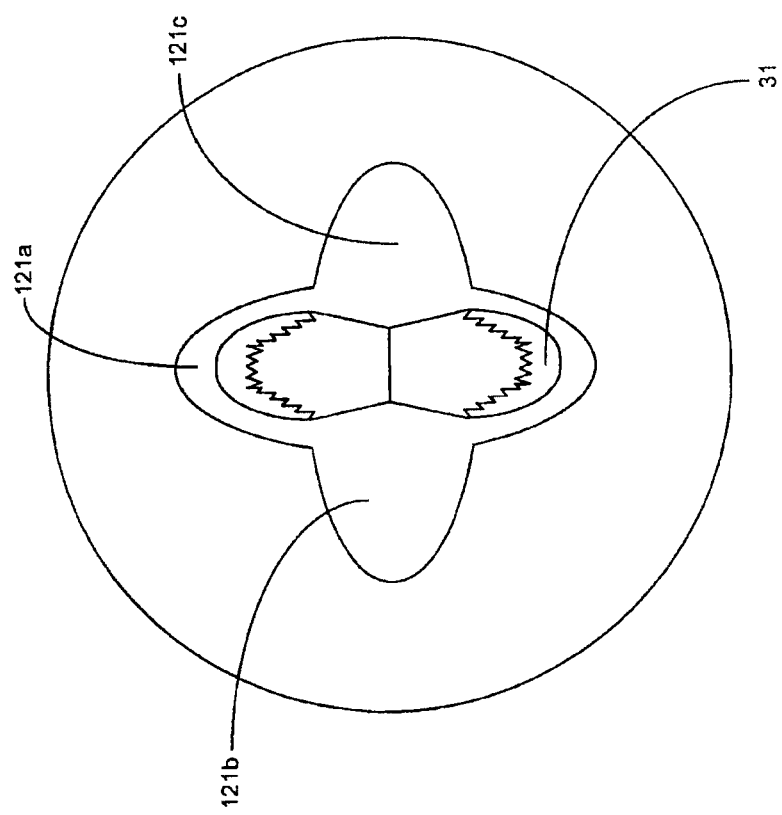
FIG. 11 is a schematic cross-sectional view of a distal portion of an endoscope and a distal assembly of an endoscopic instrument according to a yet further embodiment of the invention.

Endoscope 1 and endoscopic instrument 30 may be configured such that endoscopic instrument 30 is disposed at a particular circumferential orientation or range of circumferential orientations relative to endoscope 1. For example, chamber 130 may have a substantially oval-shape, as shown in FIG. 11, such that distal assembly 31 of endoscopic instrument 30 may be placed in an open configuration in a small range of circumferential orientations. This may be desirable, for example, such that irrigation lumen 121b and aspiration lumen 121c may be most ideally positioned relative to distal assembly 31 to remove tissue sample 32 from chamber 130. Any suitable configurations and/or structures may be used to achieve this effect. For example, working lumen 121a and/or chamber 130 may include a protrusion and the outside of endoscopic instrument 30 may include a groove configured to receive the protrusion such that the protrusion will only fit in the groove in a limited number of circumferential orientations.

Figure 12A:
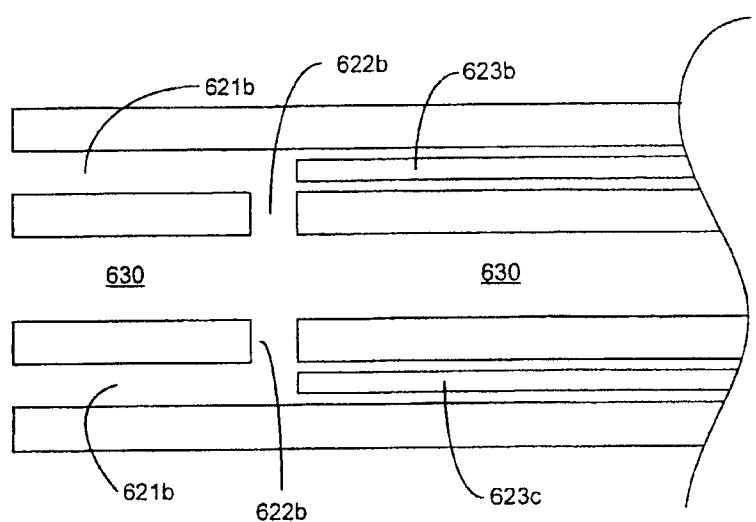
FIGS. 12A-12C are schematic cross-sectional views of a distal portion of an endoscope according to another embodiment of the invention.
Figure 12B:
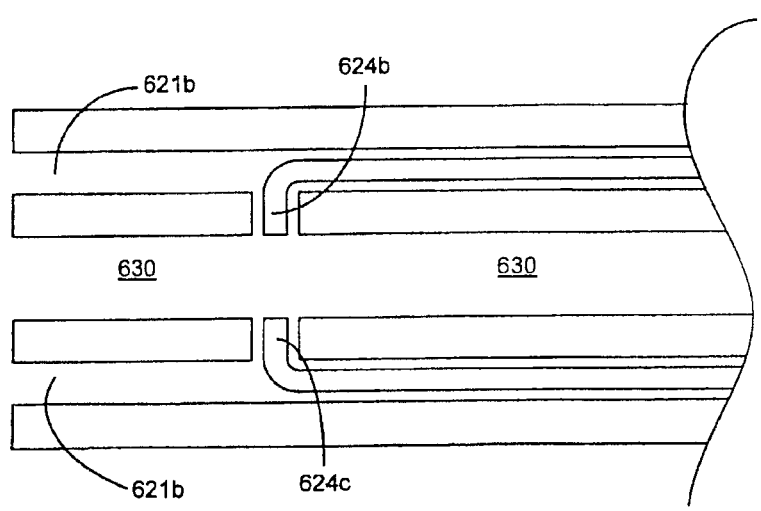
Figure 12C:
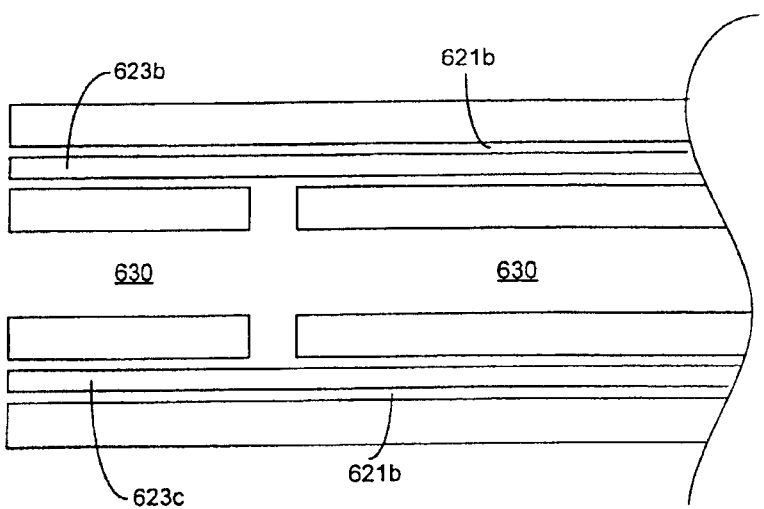

In another exemplary embodiment depicted in FIGS. 12A-12C, the endoscope may include distal chamber 630 surrounded by one or more lumens 621b. Lumens 621b may be in flow communication with distal chamber 630 via channels 622b. One or more of lumens 621b may have tubes 623b, 623c disposed therein that are longitudinally movable relative to distal chamber 630 and lumens 621b. Tubes 623b, 623c may be configured to conduct irrigation and/or aspiration, for example, tube 623b may be an irrigation tube and tube 623c may be an aspiration tube. Tubes 623b, 623c may include curved portions 624b, 624c configured, for example, to enter channels 622 and face distal chamber 630 as shown in FIG. 12B. Curved portions 624b, 624c may be flexible enough such that when moved proximally (as shown in FIG. 12A) or distally (as shown in FIG. 12C) relative to channels 622, curved portions 624b, 624c become substantially straight. In the configuration shown in FIG. 12C, tubes 623b, 623c may be configured to conduct irrigation and/or aspiration with the outside environment. Tubes 623b, 623c may be jointly and/or independently movable relative to each other, and in some embodiments, only one of tubes 623b, 623c may be deployed in lumens 621b, with the other lumen 621b conducting irrigation and/or aspiration as necessary. Tubes 623b, 623c may be actuated to attain a curved shape at portions 624b, 624c through any suitable means, such as use of a pull wire or through the material used (e.g., shape memory material).

Figure 13:
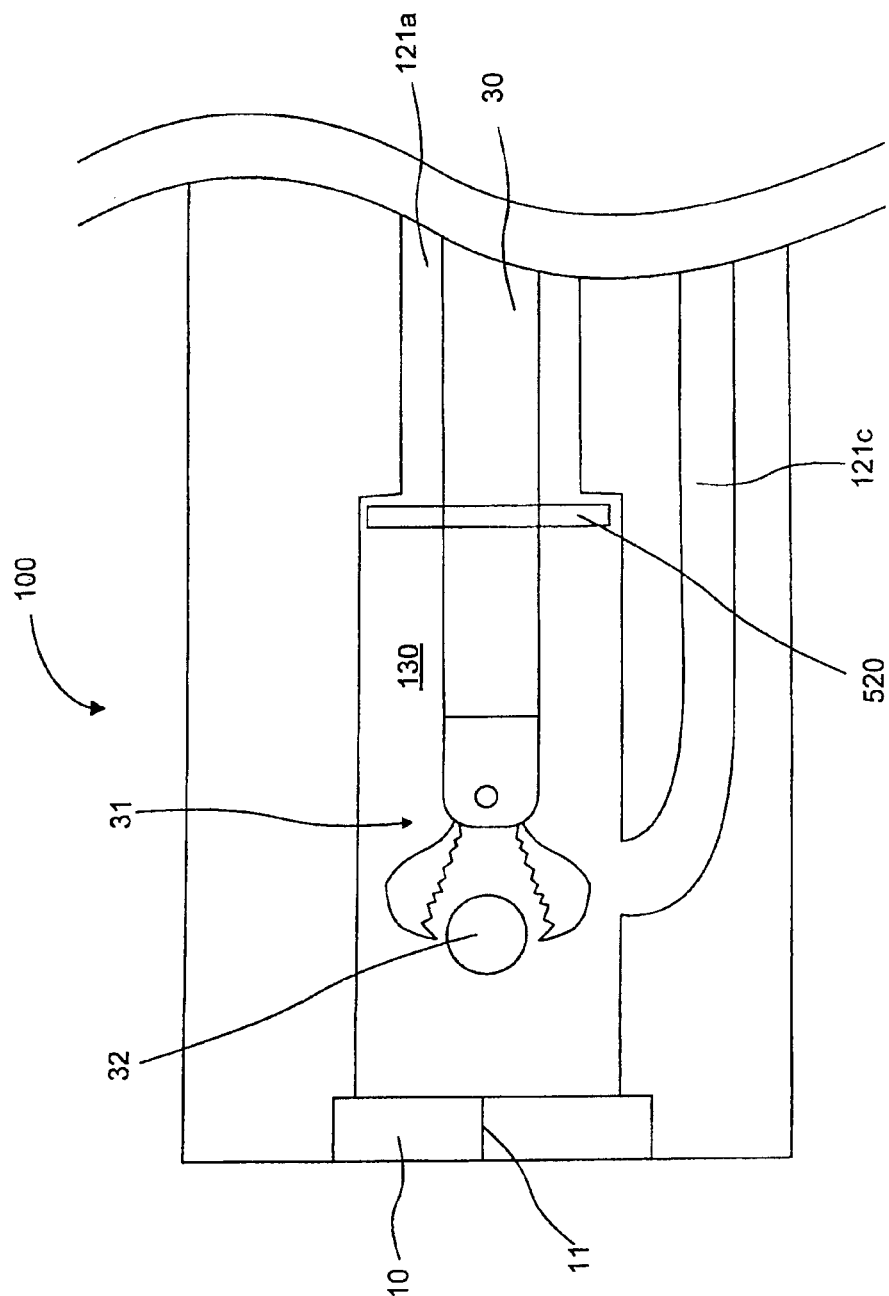
FIG. 13 is a schematic cross-sectional view of a distal portion of an endoscope and a distal assembly of an endoscopic instrument according to a further embodiment of the invention.

In various embodiments, endoscope 1 may have any number of seals on any portion of endoscope 1 and/or endoscopic instrument 30. For example, as shown in FIG. 13, seal 520 may be placed on endoscopic instrument 30 proximal to distal assembly 31. Seal 520 may cooperate with the interface between working lumen 121a and distal chamber 130 to at least partially prevent fluid flow therethrough and/or seal 520 may have a cross-sectional area substantially similar to distal chamber 130 so as to at least partially prevent fluid flow therepast.

Figure 14:
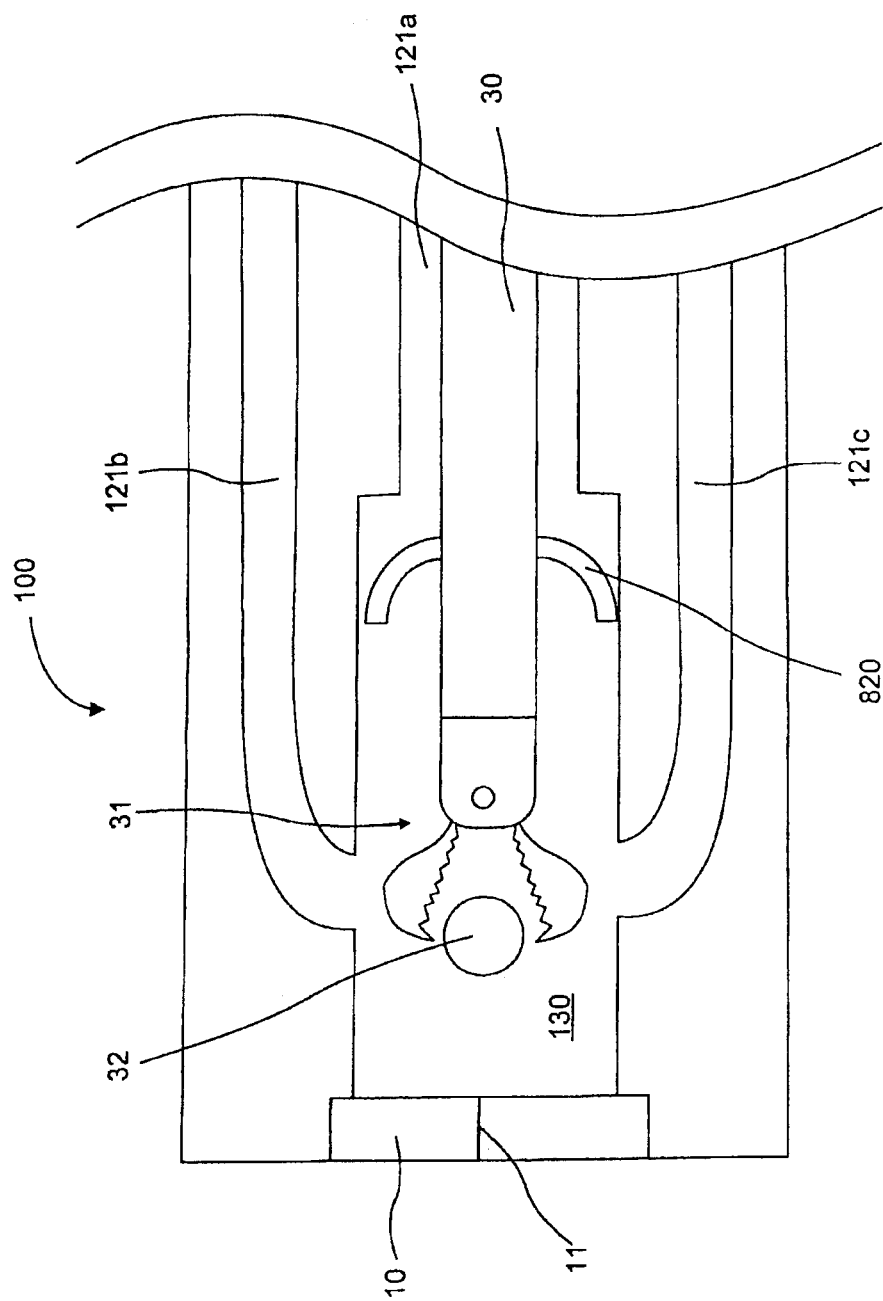
FIG. 14 is a schematic cross-sectional view of a distal portion of an endoscope and a distal assembly of an endoscopic instrument according to yet another embodiment of the invention.

Any seal set forth herein may have any suitable shape. For example, FIG. 14 depicts seal 820 having a substantially cup-shaped configuration. Such a configuration may be advantageous, for example, in at least partially preventing fluid flow therethrough from distal chamber 130 into working lumen 121a.

Figure 15A:
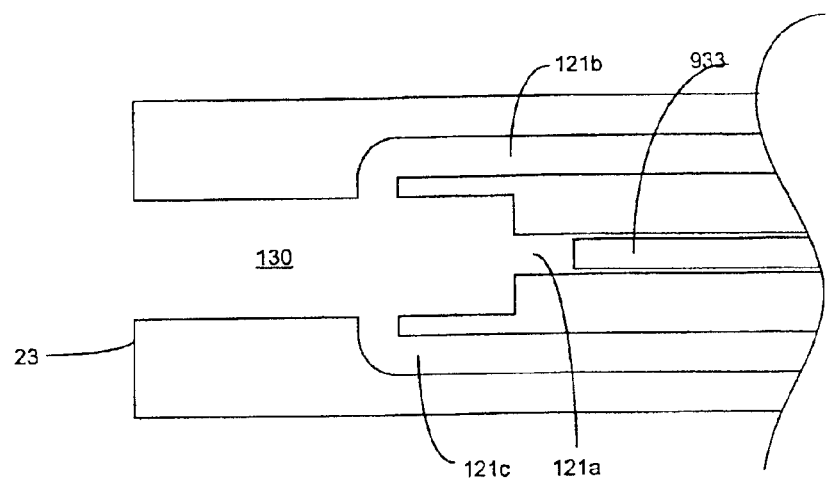
FIGS. 15A-15C are schematic cross-sectional views of a distal portion of an endoscope and a distal assembly of an endoscopic instrument according to still another embodiment of the invention.
Figure 15B:
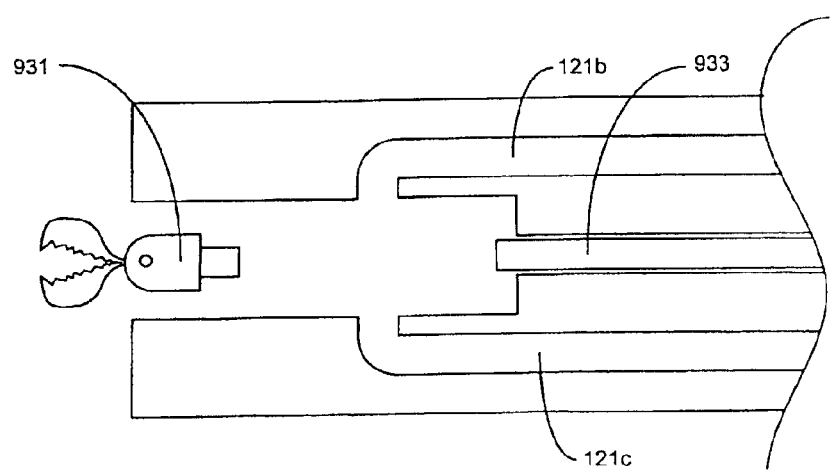
Figure 15C:
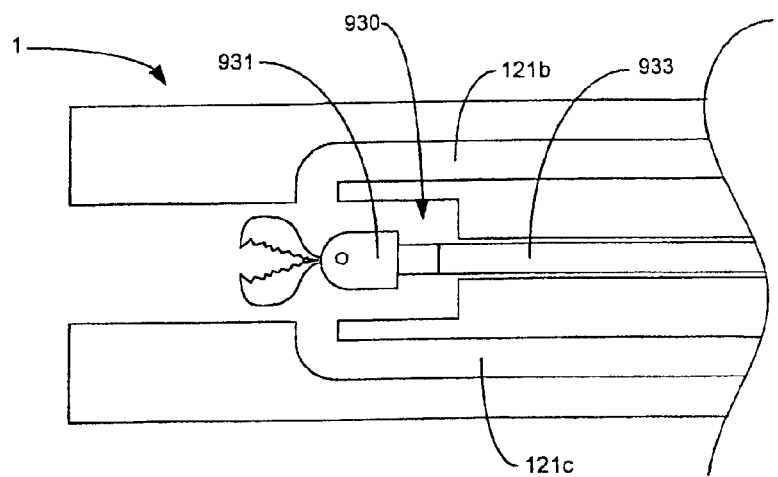

In a further embodiment, endoscopic instrument 930 may be provided in multiple pieces. For example, as shown in FIGS. 15A-15C, endoscopic instrument 930 may include elongate portion 933 and distal assembly 931 that are detachable from each other. Elongate portion 933 may be disposed in working lumen 121a. Distal assembly 931 may be introduced through distal end 23 of endoscope 1 and attached to a distal end of elongate portion 933. Distal assembly 931 may have a cross-sectional area such that it may fit within distal chamber 130, but would not fit within working lumen 121a. A proximal end of elongate portion 933 may be configured to be attached to a handle portion configured to manipulate distal assembly 931 via elongate portion 933. Examples of advantages of endoscopic instrument 930 are set forth in U.S. Patent Application Publication No. 2003/0105488 A1 published on Jun. 5, 2003, the entirety of which is incorporated herein by reference.

Figure 16:
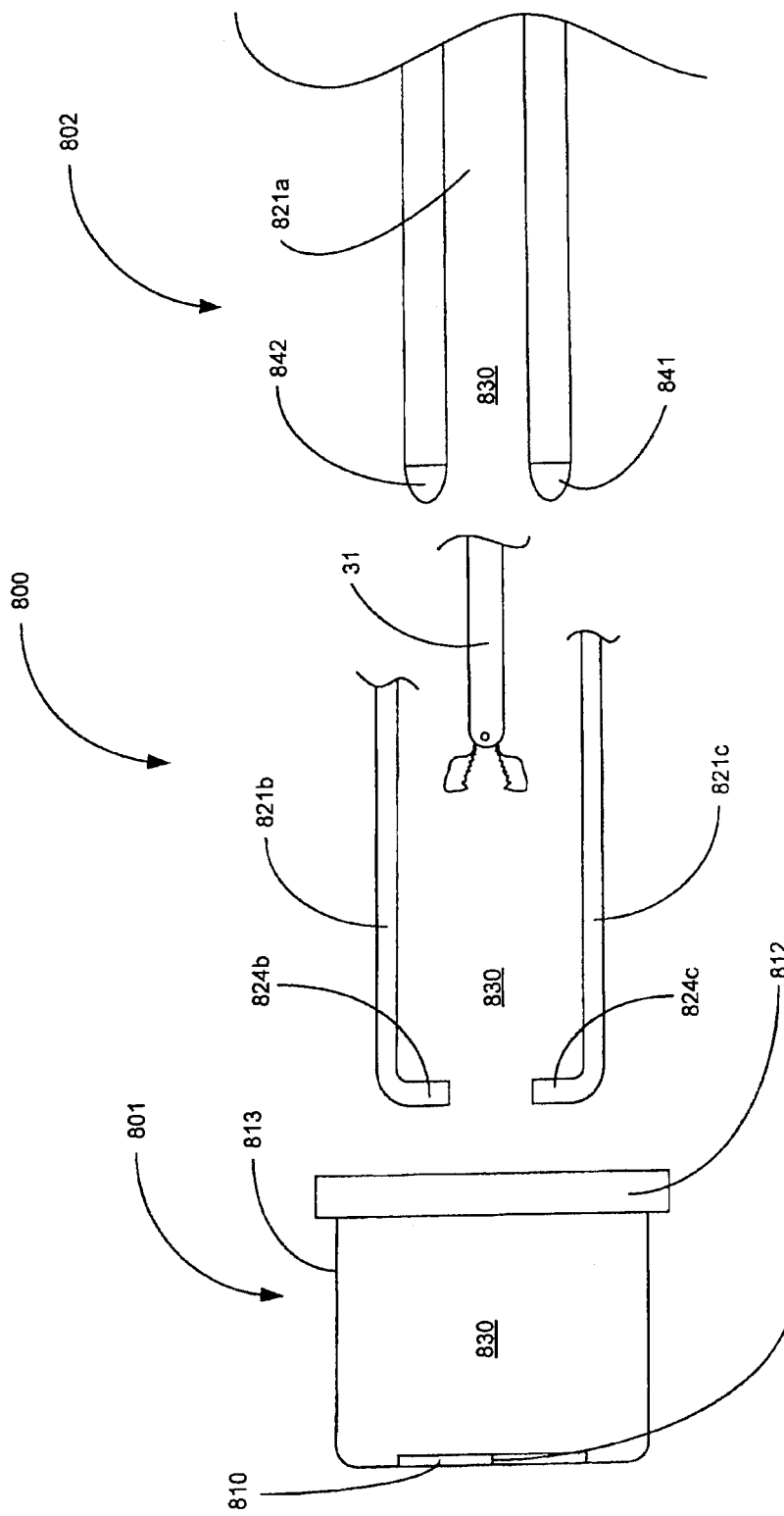
FIG. 16 is a schematic, exploded, cross-sectional view of a distal portion of an endoscope and a distal assembly of an endoscopic instrument according to a yet further embodiment of the invention.

In another embodiment, endoscopic assembly 800 may include multiple interlocking portions. For example, as shown in FIG. 16, endoscopic assembly 800 may include one or more of distal cap 801, tubes 821b, 821c configured to accommodate irrigation and/or aspiration, distal assembly 31 of endoscopic instrument 30, and endoscope 802 defining working lumen 821a. Distal cap 801 may include seal 810 with slit 811, outer housing 813 defining distal chamber 830, and attachment portion 812 configured to attach distal cap 801 to one or more of tubes 821b, 821c and endoscope 802. Attachment portion 812 may provide sufficient attachment to tubes 821b, 821c and/or endoscope 802 so as to prevent detachment due to pressures in distal chamber 830 associated with irrigation and/or aspiration. Tubes 821b, 821c may include distal portion 824b, 824c configured to curve inward so as to provide irrigation and/or aspiration to distal chamber 830 when endoscopic assembly 800 is fully assembled. Endoscope 801 may include illumination portion 842 and visualization portion 841 on its distal end that may operate by providing illumination and/or visualization through outer housing 813 of distal cap 801 either through apertures in outer housing 813, or outer housing 813 being made of a transparent material.

Figure 17:
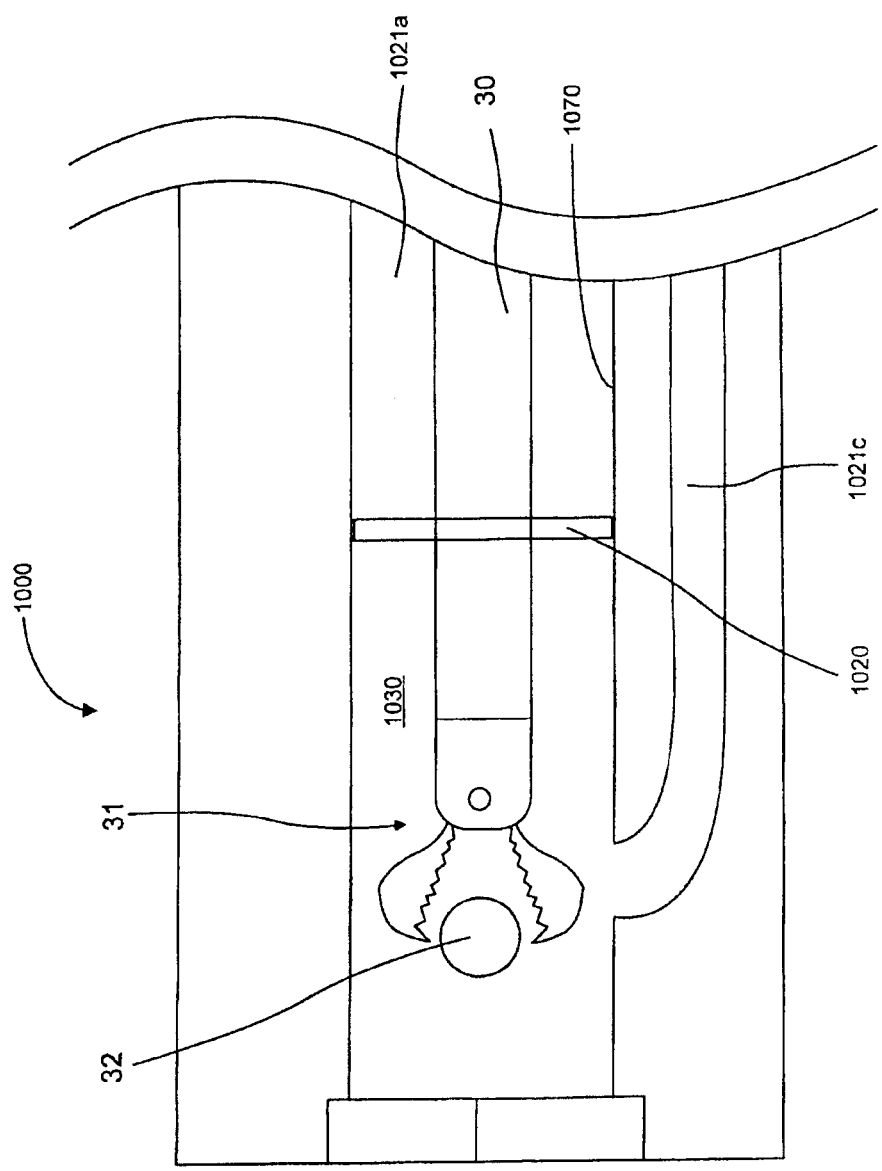
FIG. 17 is a schematic cross-sectional view of a distal portion of an endoscope and a distal assembly of an endoscopic instrument according to a still further embodiment of the invention.

In a further embodiment, endoscope 1000 may only include working lumen 1021a and aspiration lumen 1021c as shown in FIG. 17. Endoscopic instrument 30 may include a seal 1020 disposed therearound. Seal 1020 may be configured to have a cross-sectional area substantially similar to a cross-sectional area of working lumens 1021a. Seal 1020 may be configured to cooperate with inner surface 1070 of endoscope 1000 to form a substantially airtight seal such that when aspiration is conducted through aspiration lumen 1021c, enough of a vacuum is created in distal chamber 1030 such that tissue sample 32 may be aspirated out of distal chamber 1030 via aspiration lumen 1021c.

An embodiment of the invention may include a method of using an endoscope and endoscopic instrument, for example, endoscope 1 and endoscopic instrument 30 as set forth in FIGS. 1-4.

In the method, endoscope 1 may be provided, proximal end 122b of irrigation lumen 121b may be connected to a source of fluid 40, and proximal end 122c of aspiration lumen 121c may be connected to source of suction 50 and container 60, for example, as shown in FIG. 3. Using a visual image provided by viewing lumen 221, shown in FIG. 4, elongate member 20 of endoscope 1 may be advanced into a body lumen, for example, a gastrointestinal tract of a patient. Elongate member 20 may be advanced until distal end 23 and/or distal portion 100 may be substantially adjacent to a desired portion of the gastrointestinal tract, for example, a portion to be treated or a portion from which a tissue sample 32 is desired.

Once so positioned, distal assembly 31 of endoscopic instrument 30 may be advanced into working lumen 121a via proximal end 122a. Endoscopic instrument 30 may be advanced through working lumen 121a until distal assembly 31 reaches distal end 123a. Distal assembly 31 of endoscopic instrument 30 may then be advanced through second seal 120, for example, through perforation 121 and into distal chamber 130. Distal assembly 31 of endoscopic instrument 30 may then be further advanced through distal chamber 130, through first seal 110 via perforation 111, and into the gastrointestinal tract. Once disposed in the gastrointestinal tract, endoscope 1 and distal assembly 31 may be repositioned in the gastrointestinal tract, and distal assembly 31 of endoscopic instrument 30 may obtain tissue sample 32.

Once the tissue sample has been obtained, distal assembly 31 of endoscopic instrument 30 may be retracted into distal chamber 130 through perforation 111 of first seal 110. Once tissue sample 32 is disposed in distal chamber 130, sensor 140 may detect that distal assembly 31 is completely disposed within distal chamber 130, and provide audio or visual feedback to the user. Alternatively, the operator may receive a tactile feedback indicating that distal assembly 31 is in distal chamber 130. Consequently, fluid may flow into distal chamber 130 from fluid source 40 via proximal end 122b, irrigation lumen 121b, and distal end 123b, for example, for about 5 seconds at between about 60 psi and 80 psi. Distal assembly 31 of endoscopic instrument 30 may either release the tissue sample 32, as shown in FIG. 5, or the fluid flowing into distal chamber 130 from irrigation lumen 121b may dislodge tissue sample 32 from endoscopic instrument 30. Tissue sample 32 may be released into any position in distal chamber 130, for example, substantially adjacent to distal end 123c of aspiration lumen 121c. First seal 110 may substantially prevent fluid from flowing out of distal chamber 130 and into the outside environment, and second seal 120 may substantially prevent fluid from flowing out of distal chamber 130 and into working lumen 121a, for example, because second seal 120 may form a substantially fluid tight seal around endoscopic instrument 30, also as shown in FIG. 5.

Suction may be initiated from suction source 50 such that gas(es), fluid(s), and tissue sample(s) 32 may be removed from distal chamber 130 by flowing through distal end 123c, aspiration lumen 121c, and proximal end 122c into container 60, for example, at about 15 in/Hg. First seal 110 may substantially prevent the application of suction to the outside environment, and thereby prevent air from flowing into distal chamber 130 from the outside environment, and second seal 120 may substantially prevent fluid from flowing into distal chamber 130 from working lumen 121a, for example, because second seal 120 may form a substantially airtight seal around endoscopic instrument 30.

Once the tissue sample(s) 32, gas(es), and/or fluid(s) have been removed from distal chamber 130, distal assembly 31 of endoscopic instrument 30 may be advanced back into the outside environment through perforation 111 of first seal 110 and another tissue sample 32 may be acquired. Distal assembly 31 of endoscopic instrument 30 may then again be retracted into distal chamber 130 and tissue sample 32 may be irrigated via fluid from fluid source 40 and aspirated to container 60 using any step or steps set forth herein. Any combination of any of these steps may be repeated as many times as desired to obtain as many tissue samples as desired.

Once the desired number of tissue samples 32 have been obtained, endoscopic instrument 30 may be retracted out of first seal 110, distal chamber 130, second seal 120, distal end 123a, working lumen 121a, and proximal end 122a. Elongate member 20 of endoscope 1 may then be removed from the gastrointestinal tract.

Endoscope 1 may be used in any suitable medical procedure in any suitable portion of the body. Endoscopic instrument 30 may be any suitable endoscopic instrument to perform any desired endoscopic procedure, whether to obtain tissue samples 32 or otherwise. For example, endoscopic instrument 30 may include any suitable instrument manufactured and/or sold by BOSTON SCIENTIFIC CORPORATION™ or its subsidiaries, for example, a RADIAL JAW 3 BIOPSY FORCEPS™ or RADIAL JAW 4 BIOPSY FORCEPS™.

Figure 6:
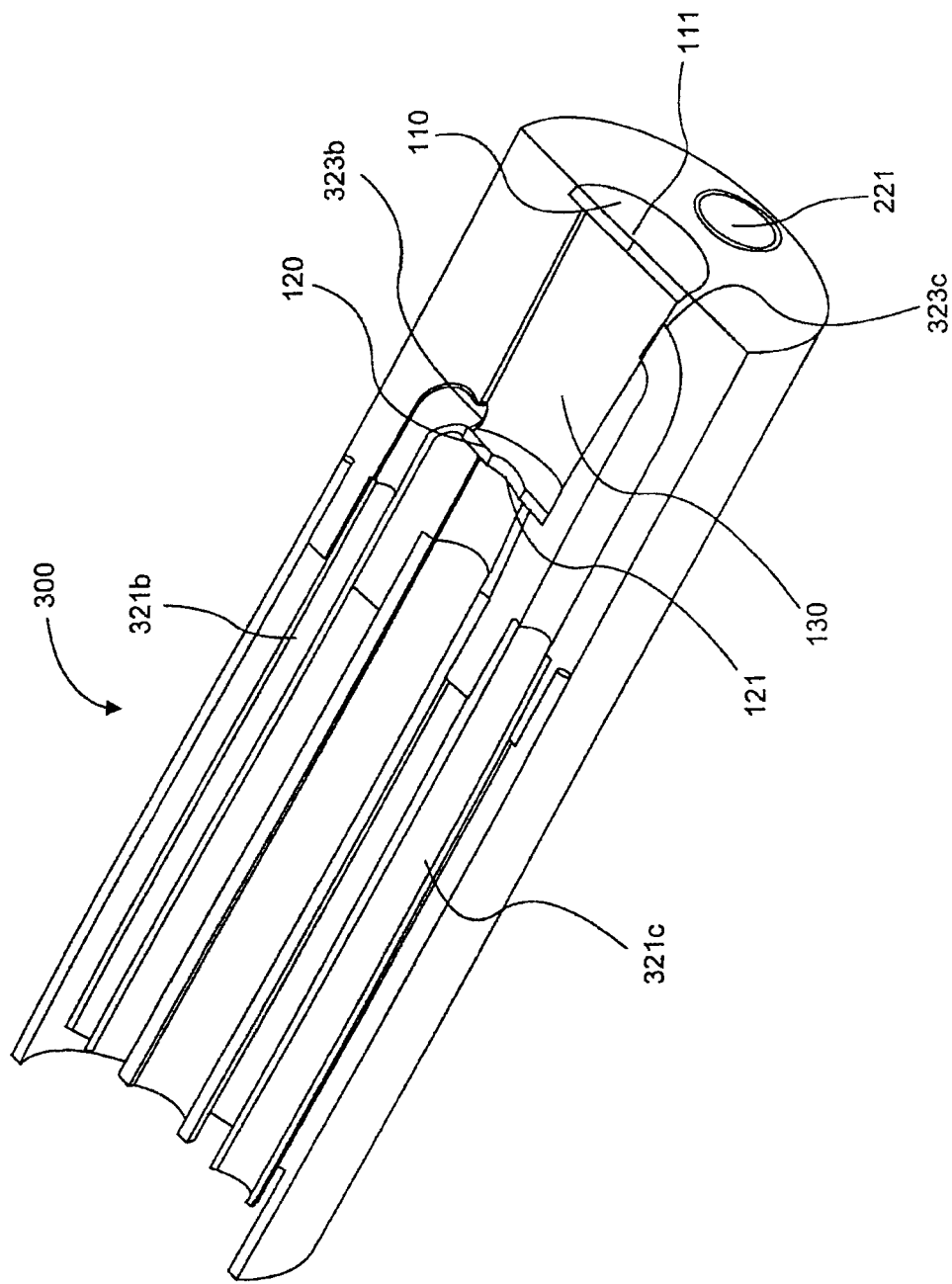
FIG. 6 is a schematic cross-sectional view of a distal portion of an endoscope according to another embodiment of the invention.

Distal assembly 100 of endoscope 1 may have alternative embodiments. For example, FIG. 2 shows a distal portion 100 wherein distal ends 123b, 123c of irrigation lumen 121b and aspiration lumen 121c are substantially facing each other. However, in distal portion 300 as shown in FIG. 6, distal ends 323b, 323c of lumens 321b, 321c may be disposed at different portions of distal chamber 130 such that they do not face each other. For example, distal end 323b may be disposed at a proximal end (e.g., closer to second seal 120) of distal chamber 130 while distal end 323c may be disposed at a distal end (e.g., closer to first seal 110) of distal chamber 130. Lumens 321b, 321c may be any combination of an irrigation lumen and an aspiration lumen. For example, lumen 321b may be an irrigation lumen and lumen 321c may be an aspiration lumen, such that fluid will flow into distal chamber 130 from distal end 323b of irrigation lumen 321b and distally push tissue sample 32 to distal end 323c of aspiration lumen 321c.

In various embodiments, endoscope 1 may have any number of lumens 21 with any number of distal ends located in any portion of distal chamber 130. Each distal end of various lumens may have any shape, size, or configuration, and any two distal ends of lumens 21 may have either the same shapes, sizes, and configurations, or different shapes, sizes, and configurations. A single lumen 21 may even have more than one distal end in distal chamber 130. The distal ends of lumens 21 may enter distal chamber 130 at any suitable angle, in both the axial and radial planes. The distal ends of lumens 21 may be configured about distal chamber 130 to achieve a specific flow profile, for example, turbulent flow or chaotic flow in distal chamber 130.

Figure 7:
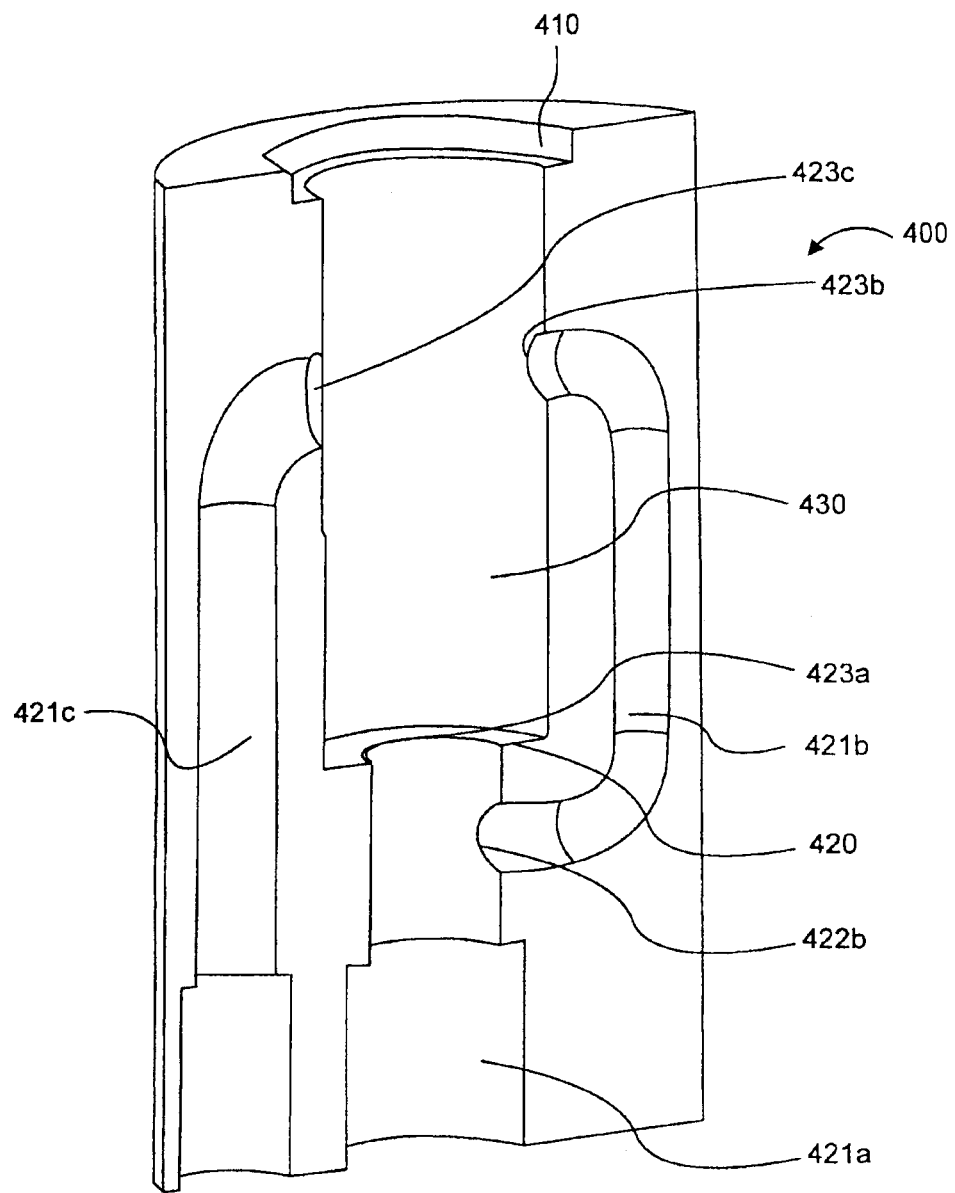
FIG. 7 is a schematic view of a distal portion of an endoscope according to a further embodiment of the invention.
Figure 8:
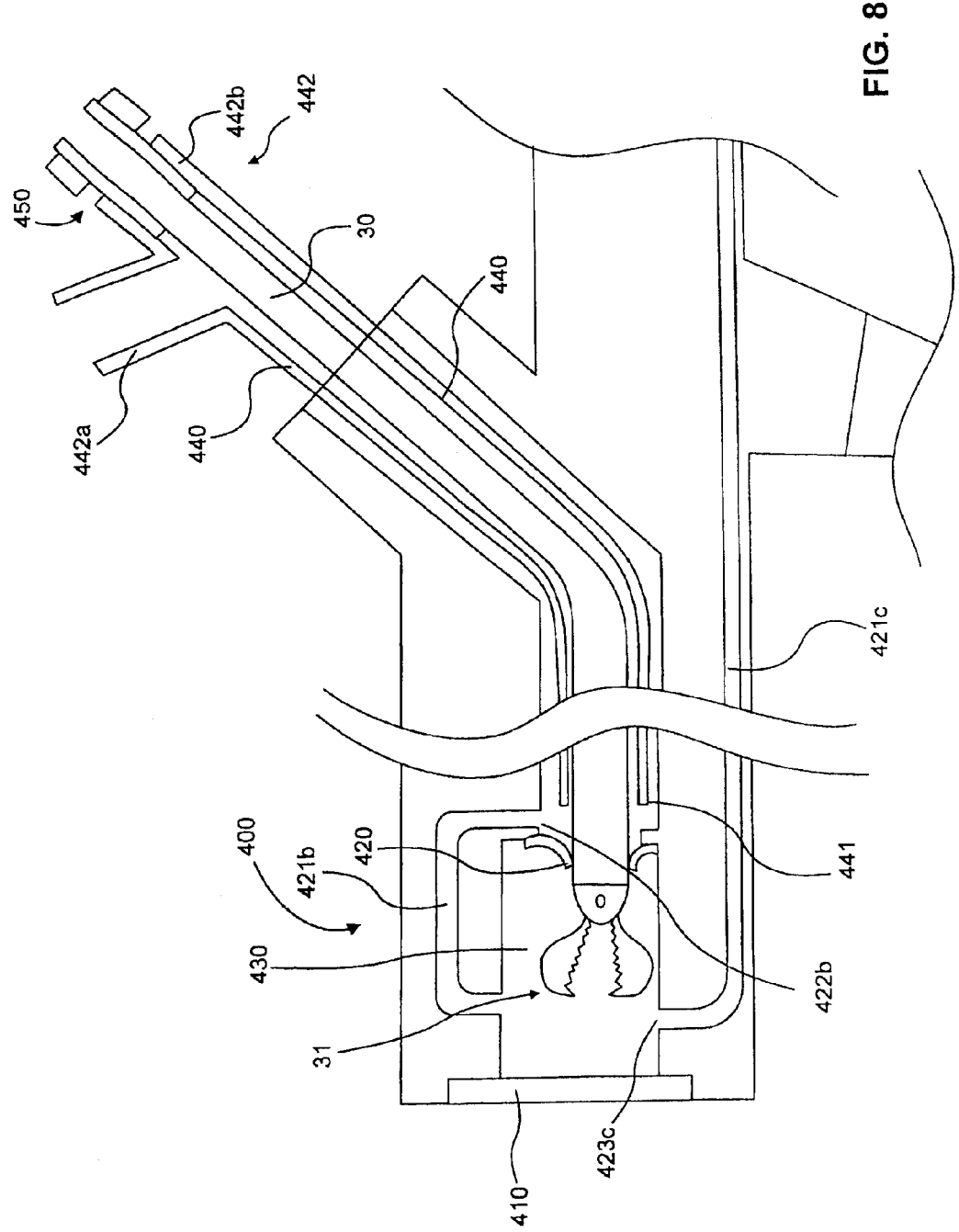
FIG. 8 is a schematic view of an endoscope and a biopsy instrument therein, according to still another embodiment of the invention and the distal portion of FIG. 7.

In another embodiment, FIGS. 7-8 show a distal portion 400 including an irrigation fluid bypass 421b (i.e., irrigation lumen) with a proximal end 422b connected to working lumen 421a proximal to distal end 423a. Distal ends 423b, 423c of irrigation lumen 421b and aspiration lumen 421c may be connected to and/or be in flow communication with distal chamber 430 in any suitable configuration, for example, between first seal 410 and second seal 420. Accordingly, fluid source 40 may be connected to a proximal end 122a of working lumen 421a. When in operation, fluid may flow from fluid source 40, through proximal end 122a, through working lumen 421a, and come up against second seal 420. At this point, second seal 420 may or may not have an endoscopic instrument 30 disposed therethrough. In any case, fluid from working lumen 421a may be directed (e.g., by second seal 420) through proximal end 422b of water bypass 421b and into distal chamber 430 via distal end 423b.

As shown in FIG. 8, fluid may flow to distal portion 400 via an elongate sheath 440 disposed around an elongate portion of endoscopic instrument 30. A distal end 441 of elongate sheath 440 may be disposed proximal to distal chamber 430 and second seal 420, and proximal or adjacent to proximal end 422b of irrigation lumen 421b such that fluid may flow from elongate sheath 440 into irrigation lumen 421b via proximal end 422b. A proximal portion 442 of elongate sheath 440 may include a Y-connector (e.g., manufactured by QOSINA™) including a plurality of lumens 442a, 442b. Lumen 442a may be configured to be connected to a source of fluid 40. Lumen 442b may be configured to receive endoscopic instrument 30 and may include a connector 450 (e.g., a Touhy-Borst connector manufactured by QOSINA™) on a proximal end.

Connector 450 may be configured such that in a first configuration, endoscopic instrument 30 may move freely longitudinally relative to elongate sheath 440, for example, while distal assembly 31 is being moved relative to distal chamber 430 so as to acquire tissue sample 32 and place tissue sample 32 in distal chamber 430. Connector 450 may be placed in a second configuration so as to prevent endoscopic instrument 30 from longitudinally moving relative to elongate sheath 440, for example, by locking endoscopic instrument 30 to the portion of elongate sheath 440 defining lumen 442b. At this time, connector 450 may also form a substantially fluid-tight seal so as prevent fluid from flowing proximally between elongate sheath 440 and endoscopic instrument 30 at proximal portion 442. Fluid may then be flowed through elongate sheath 440 from a fluid source 40 via lumen 442a. Fluid may be prevented from flowing proximally past lumen 442b by a combination of connector 450, elongate sheath 440, and endoscopic instrument 30. Fluid may thus flow down elongate sheath 440 and out distal end 441 into working lumen 421a and/or irrigation lumen 421b. Fluid may flow from there into distal chamber 430 so as to float and/or carry tissue sample 32 toward distal end 423c of aspiration lumen 421c, and eventually sent to container 60. An advantage to this configuration may be that space is saved and/or manufacturing of endoscope 1 becomes less complicated due to the elimination of an irrigation lumen running an entire length of the elongate portion 20 of endoscope 1.

Figure 9:
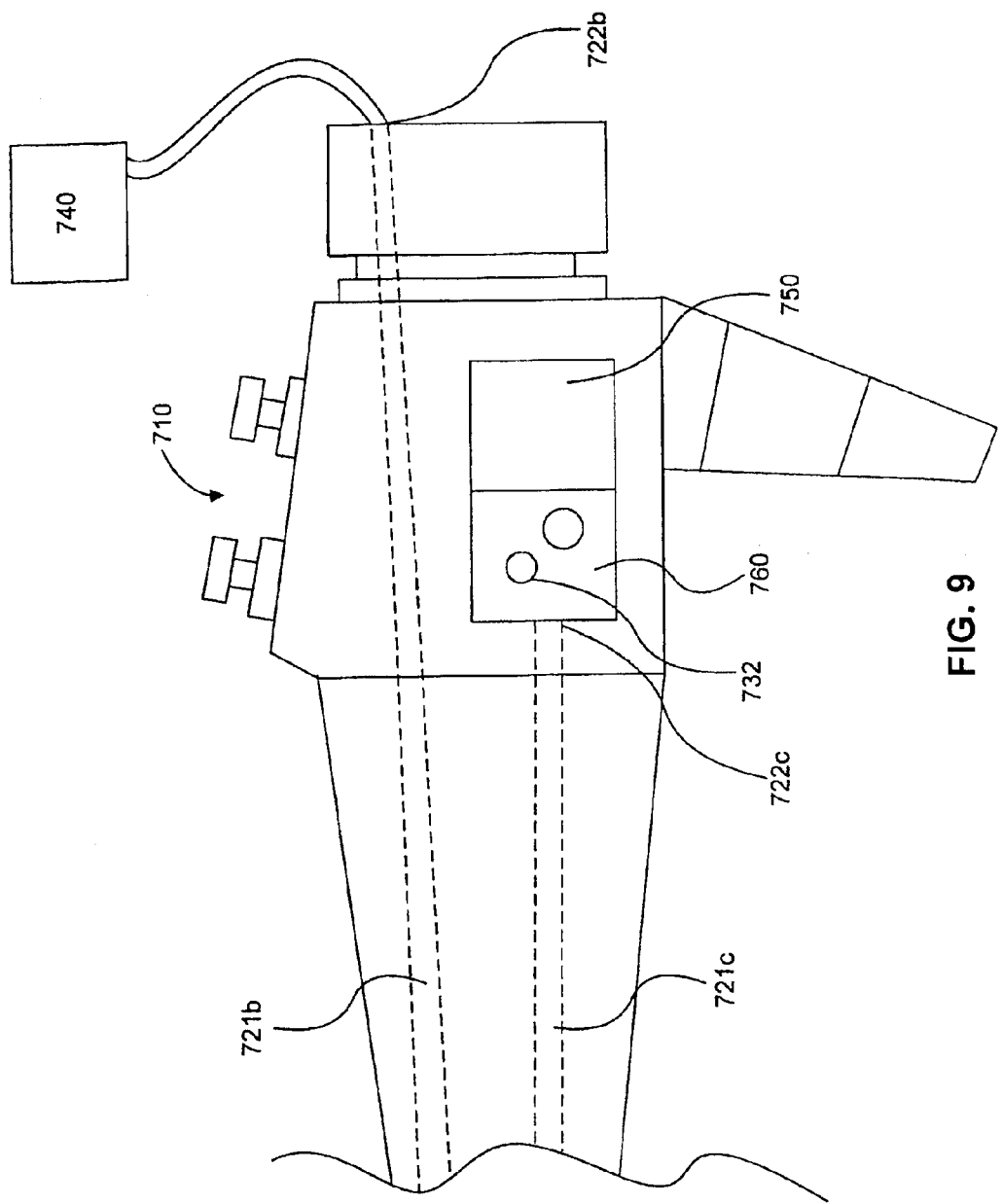
FIG. 9 is a schematic view of a handle portion of an endoscope according to yet another embodiment of the invention.

In a further embodiment, FIG. 9 depicts a handle portion 710 configured to be connected to a source of fluid 740 and also including both a source of suction 750 and a container 760 for storing tissue samples 732. Container 760 may either be removable from handle portion 710, or container 760 may be configured to allow tissue samples 732 to be removed from container 760, for example, by including a door or other means to access the samples 732. Proximal end 722b of irrigation lumen 721b may be attached to fluid source 740, and proximal end 722c of aspiration lumen 721c may be attached to any combination and/or configuration of suction source 750 and container 760. Other examples of suitable devices and/or configurations for storing and removing tissue samples are set forth in U.S. Pat. No. 6,926,676 B2 issued Aug. 9, 2005 to Vincent TURTURRO et al, the entirety of which is incorporated herein by reference.

Any aspects of any of the embodiments set forth herein may be combined in any suitable combination. For example, distal assembly 100 may include a proximal end 22 as set forth in FIG. 3 and/or a handle portion 710 as set forth in FIG. 9. In another example, endoscope 1 may include any of distal portions 100, 300, or 400.

Any suitable part may be used for any aspect set forth herein and may have any suitable size, shape, and/or configuration. For example, the portion of the aspiration lumen disposed in the elongate member of the endoscope proximal to the distal portion may be a ARKEMA PEBAX 7233 SN 01 Polyether Block Amide having an inner diameter of about 0.07 inches, an outer diameter of about 0.09 inches, and a length of about 240 cm. In a further example, the portion of the irrigation lumen disposed in the elongate member of the endoscope proximal to the distal portion may be manufactured by ENDOVATIONS™. In another example, the endoscope may be made of PELLETHANE 55D RESIN and have an inner diameter if about 0.11 inches, an outer diameter of about 0.15 inches, and a length of about 190 cm. In yet another example, the source of suction may be a suction pump manufactured by MEDICAL SPECIFICS.

Figure 18A:
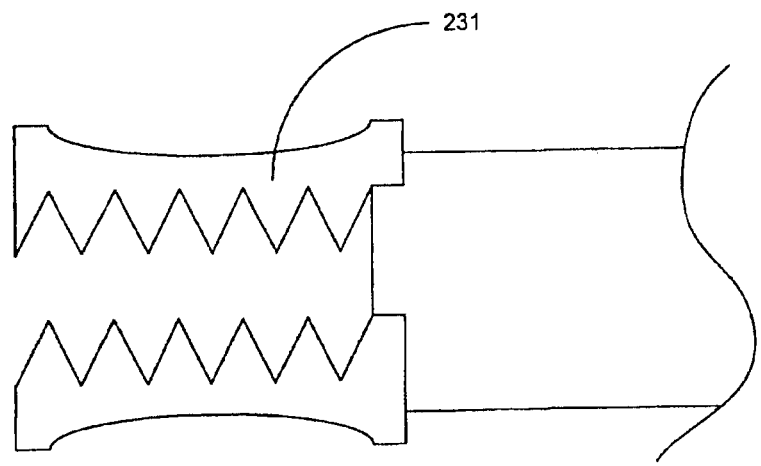
FIGS. 18A-18B are schematic cross-sectional views of a distal assembly of an endoscopic instrument according to another embodiment of the invention.
Figure 18B:
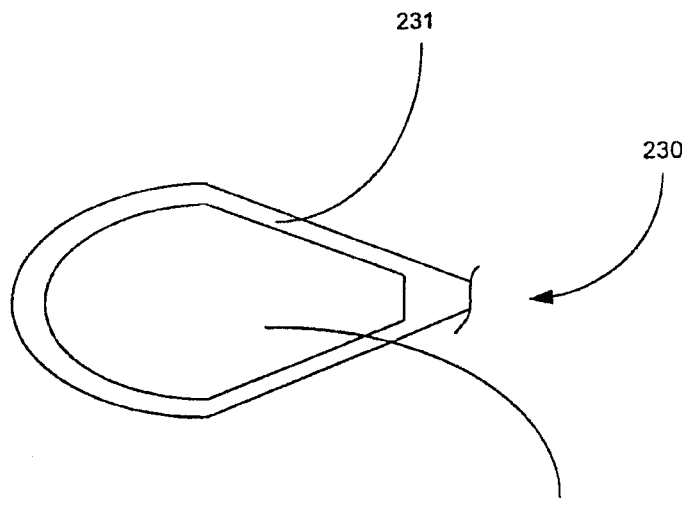

Any suitable device may be used in conjunction with endoscope 1. For example, endoscopic instrument 30 may be any medical instrument including, but not limited to, biopsy forceps, baskets, graspers, snares, and/or needles. An example of an endoscopic instrument 230 is set forth in FIGS. 18A-18B. Endoscopic instrument 230 includes distal forceps 231 including apertures 232 extending through distal forceps 231. Accordingly, in operation, forceps 231 may be used to acquire tissue which then may be disposed in apertures 232. Forceps 231 may then be placed in distal chamber 130 as set forth in FIGS. 1-4 in an orientation such that apertures 232 are substantially in line with distal ends 123b, 123c of irrigation and aspiration lumens 121b, 121c. Fluid may then be run through irrigation lumen 121b into distal chamber 130 and through apertures 232 to dislodge the acquired tissue sample. The tissue sample may then be aspirated by aspiration lumen 121c. In some embodiments, the fluid pressure from irrigation lumen 121b and/or vacuum pressure from aspiration lumen 121c may be sufficient to dislodge the tissue from forceps 231, either through apertures 232 or directly from the teeth of forceps 231, without opening forceps 231 or only partially opening forceps 231.

There are many advantages to the various embodiments set forth in this application. For example, multiple tissue samples may be acquired without removing endoscopic instrument 30 and particularly its distal assembly 31, from endoscope 1. As a result, more tissue samples may be acquired in less time. There also is less risk of cross-contamination of samples, as compares to a prior method of stacking multiple samples within the biopsy jaws. In addition, there is less risk of contamination and infection due to continually removing and reinserting endoscopic instrument 30.

In various embodiments, the invention may include providing a kit where an endoscopic instrument 30 is already disposed in endoscope 1. Distal assembly 31 may be disposed in distal chamber 130 such that a user may purchase the kit with endoscopic instrument 30 already disposed in endoscope 1, and immediately use the kit by advancing endoscope 1 into the body. Such a kit may be advantageous because it reduces the number of steps in an endoscopic procedure, i.e., the step of advancing the endoscope instrument 30 through endoscope 1. In some embodiments, distal assembly 31 may be integrated with endoscope 1 in distal chamber 130, and only pull wires or other actuations means may be disposed the length of endoscope 1, for example, through working lumen 121a.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscope, comprising:
an elongate member;
at least two lumens extending through the elongate member; and
a chamber defined by a distal portion of the elongate member, the chamber normally closed at a distal end of the chamber, and wherein the distal end of the chamber is configured to selectively receive a medical instrument therethrough;
wherein a distal end of each of the at least two lumens terminates in the chamber.

2. The endoscope of claim 1, wherein the chamber includes a first seal at a distal end of the chamber and a second seal at a proximal end of the chamber, and
wherein the chamber is located along a central longitudinal axis of the elongate member.

3. The endoscope of claim 1, wherein the chamber is configured to accommodate a distal assembly of the medical instrument.

4. The endoscope of claim 1, wherein the endoscope further includes a working channel, and a distal portion of each of the at least two lumens is curved relative to a remainder of the at least two lumens.

5. The endoscope of claim 1, wherein a distal end of a first lumen of the at least two lumens includes a diameter larger than a remainder of the first lumen, and wherein a distal end of the second lumen of the at least two lumens includes a diameter smaller than a remainder of the second lumen.

6. The endoscope of claim 1, further comprising a sensor configured to determine when an endoscopic tool is disposed within the chamber.

7. An endoscope, comprising:
an elongate member;
an irrigation lumen and an aspiration lumen extending through the elongate member; and
a chamber defining an unoccupied space and defined by a distal portion of the elongate member,
wherein a distal end of each of the irrigation lumen and the aspiration lumen terminates in the chamber,
wherein a distal end of the chamber is configured to selectively receive a medical instrument therethrough and wherein the chamber is further configured to accommodate a distal assembly of the medical instrument.

8. The endoscope of claim 7, wherein the distal ends of each of the irrigation lumen and the aspiration lumen are at an angle relative to a longitudinal axis of the elongate member.

9. The endoscope of claim 7, wherein the chamber includes a first seal at a distal end of the chamber and a second seal at a proximal end of the chamber.

10. The endoscope of claim 7, wherein at least one of the irrigation lumen and the aspiration lumen includes a valve configured to selectively provide irrigation or aspiration, respectively, to either the chamber or a body lumen.

11. The endoscope of claim 7, wherein a distal end of at least one of the irrigation lumen and the aspiration lumen includes a nozzle-like configuration or a flare-like configuration.

12. The endoscope of claim 7, wherein the chamber is normally closed at a distal end of the chamber.

13. The endoscope of claim 7, wherein the chamber defines a space within the chamber when the chamber does not include a medical instrument.

14. An endoscope, comprising:
an elongate member;
an irrigation lumen extending through the elongate member; and
a chamber defining an unoccupied space and defined by a distal portion of the elongate member,
wherein a distal end of the irrigation lumen terminates in the chamber,
wherein a distal end of the chamber is configured to selectively receive a medical instrument therethrough and wherein the chamber is further configured to accommodate a distal assembly of the medical instrument.

15. The endoscope of claim 14, wherein the chamber includes a first seal at a distal end of the chamber and a second seal at a proximal end of the chamber.

16. The endoscope of claim 14, wherein the chamber includes a first seal at a distal end of the chamber and a second seal on the medical instrument.

17. The endoscope of claim 14, further comprising a sensor configured to detect an entrance of the distal assembly into the chamber.

18. The endoscope of claim 14, wherein a distal end of the irrigation lumen includes a nozzle-like configuration.

19. The endoscope of claim 14, wherein the chamber is normally closed at a distal end of the chamber.

20. The endoscope of claim 14, wherein the chamber defines a space within the chamber when the chamber does not include a medical instrument.

21. An endoscope, comprising:
an elongate member;
at least two lumens extending through the elongate member; and
a chamber defined by a distal portion of the elongate member, the chamber normally closed at a distal end of the chamber and wherein the distal end of the chamber is configured to selectively receive a medical instrument therethrough;
wherein a distal end of each of the at least two lumens terminates in the chamber,
wherein a seal is disposed between a distal end of at least one of the at least two lumens and the chamber.

22. The endoscope of claim 21, wherein the endoscope further includes a working channel, and a distal portion of each of the at least two lumens is curved relative to a remainder of the at least two lumens.

23. The endoscope of claim 21, further comprising a sensor configured to determine when an endoscopic tool is disposed within the chamber.

24. An endoscope, comprising:
an elongate member;
at least two lumens extending through the elongate member; and
a chamber defining an unoccupied space and defined by a distal portion of the elongate member;
wherein a distal end of each of the at least two lumens terminates in the chamber,
wherein the chamber includes a first seal at a distal end of the chamber and a second seal at a proximal end of the chamber and wherein the distal end of the chamber is configured to selectively receive a medical instrument therethrough.

25. The endoscope of claim 24, wherein the chamber is normally closed at a distal end of the chamber.

26. The endoscope of claim 24, wherein the chamber defines a space within the chamber when the chamber does not include a medical instrument.

* * * * *